US011090294B2

(12) United States Patent
Baker et al.

(10) Patent No.: US 11,090,294 B2
(45) Date of Patent: Aug. 17, 2021

(54) COMBINATIONS OF A MUSCARINIC RECEPTOR ANTAGONIST AND A BETA-2 ADRENORECEPTOR AGONIST

(71) Applicant: Glaxo Group Limited, Middlesex (GB)

(72) Inventors: Darrell Baker, Uxbridge (GB); Mark Bruce, Stevenage (GB); Glenn Crater, Mississauga (CA); Brian Noga, Durham, NC (US); Marian Thomas, Ware (GB); Patrick Wire, Durham, NC (US)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 15/678,246

(22) Filed: Aug. 16, 2017

(65) Prior Publication Data

US 2018/0008582 A1 Jan. 11, 2018

Related U.S. Application Data

(63) Continuation of application No. 14/970,945, filed on Dec. 16, 2015, now Pat. No. 9,750,726, which is a continuation of application No. 13/510,962, filed as application No. PCT/EP2010/068429 on Nov. 29, 2010, now abandoned.

(30) Foreign Application Priority Data

Dec. 1, 2009 (GB) .................................. 0921075.8

(51) Int. Cl.
| | |
|---|---|
| *A01N 43/00* | (2006.01) |
| *A61K 31/33* | (2006.01) |
| *A61K 31/439* | (2006.01) |
| *A61K 31/138* | (2006.01) |
| *A61K 45/06* | (2006.01) |
| *A61K 9/00* | (2006.01) |
| *B65D 75/36* | (2006.01) |

(52) U.S. Cl.
CPC .......... *A61K 31/439* (2013.01); *A61K 9/0075* (2013.01); *A61K 31/138* (2013.01); *A61K 45/06* (2013.01); *B65D 75/36* (2013.01)

(58) Field of Classification Search
CPC ... A61K 31/439; A61K 9/0075; A61K 31/138
See application file for complete search history.

(56) References Cited

U.S. PATENT DOCUMENTS

| | | |
|---|---|---|
| 4,778,054 A | 10/1988 | Newell et al. |
| 4,811,731 A | 3/1989 | Newell et al. |
| 4,832,880 A | 5/1989 | Staniforth |
| 4,994,276 A | 1/1991 | Baichwal et al. |
| 5,004,614 A | 4/1991 | Staniforth |
| 5,035,237 A | 7/1991 | Newell et al. |
| 5,135,757 A | 8/1992 | Baichwal et al. |
| 5,145,684 A | 9/1992 | Liversidge et al. |
| 5,376,386 A | 12/1994 | Ganderton et al. |
| 5,441,060 A | 8/1995 | Rose et al. |
| 5,478,578 A | 12/1995 | Arnold et al. |
| 5,503,662 A | 4/1996 | Berger |
| 5,506,203 A | 4/1996 | Blackstrom et al. |
| 5,560,490 A | 10/1996 | Chawla |
| 5,590,645 A | 1/1997 | Davies et al. |
| 5,626,871 A | 5/1997 | Makino et al. |
| 5,642,728 A | 7/1997 | Anderson et al. |
| 5,663,198 A | 9/1997 | Reul et al. |
| 5,730,785 A | 3/1998 | Idol et al. |
| 5,746,937 A | 5/1998 | McKedy et al. |
| 5,829,434 A | 11/1998 | Ambrosio et al. |
| 5,860,419 A | 1/1999 | Davies et al. |
| 5,873,360 A | 2/1999 | Davies et al. |
| 5,972,388 A | 10/1999 | Sakon et al. |
| 6,032,666 A | 3/2000 | Davies et al. |
| 6,103,141 A | 8/2000 | Incorvia et al. |
| 6,119,853 A | 9/2000 | Garrill et al. |
| 6,132,394 A | 10/2000 | Lankinen |
| 6,153,224 A | 11/2000 | Staniforth |
| 6,153,322 A | 11/2000 | Lee et al. |
| 6,156,231 A | 12/2000 | McKedy |
| 6,179,118 B1 | 1/2001 | Garrill et al. |
| D440,874 S | 4/2001 | Shurtleff et al. |
| 6,221,338 B1 | 4/2001 | Staniforth |
| 6,279,736 B1 | 8/2001 | Hekal |
| 6,315,112 B1 | 11/2001 | Garrill et al. |
| 6,321,747 B1 | 11/2001 | Dmitrovic et al. |
| 6,352,152 B1 | 3/2002 | Anderson et al. |
| 6,378,519 B1 | 4/2002 | Davies et al. |
| 6,378,579 B1 | 4/2002 | Giltner |
| 6,390,291 B1 | 5/2002 | Garrill et al. |
| 6,521,260 B1 | 2/2003 | Staniforth |
| 6,533,321 B2 | 3/2003 | Class et al. |
| 6,536,427 B2 | 3/2003 | Davies et al. |
| 6,537,983 B1 | 3/2003 | Biggadike et al. |
| 6,582,678 B2 | 6/2003 | Staniforth |
| 6,679,374 B2 | 1/2004 | Garrill et al. |
| 6,759,398 B2 | 7/2004 | Biggadike |
| 6,792,945 B2 | 9/2004 | Davies et al. |

(Continued)

FOREIGN PATENT DOCUMENTS

| | | |
|---|---|---|
| CA | 2347856 | 5/2000 |
| DE | 10056855 A1 | 5/2002 |
| DE | 202005002409 U1 | 7/2005 |
| DE | 202005004659 U1 | 7/2005 |
| EP | 0069715 A1 | 1/1983 |

(Continued)

OTHER PUBLICATIONS

Aaron et al., Tiotropium in combination with placebo, salmeterol, or fluticasone-salmeterol for treatment of chronic obstructive pulmonary disease: a randomized trial. Ann Intern Med. Apr. 17, 2017;146(8):545-55.

(Continued)

*Primary Examiner* — Jean P Cornet
(74) *Attorney, Agent, or Firm* — James P. Riek

(57) ABSTRACT

Combinations of a muscarinic acetylcholine receptor antagonist and a beta 2 agonist for inhaled administration via the nose or mouth, and methods of using them are provided.

56 Claims, No Drawings

(56) References Cited

U.S. PATENT DOCUMENTS

| | | |
|---|---|---|
| 6,878,698 B2 | 4/2005 | Biggadike et al. |
| 7,011,818 B2 | 3/2006 | Staniforth |
| 7,101,866 B2 | 9/2006 | Biggadike et al. |
| 7,186,401 B2 | 3/2007 | Keller et al. |
| 7,225,808 B2 | 6/2007 | Davies et al. |
| 7,337,593 B2 | 3/2008 | Blum et al. |
| 7,361,787 B2 | 4/2008 | Box et al. |
| 7,389,775 B2 | 6/2008 | Davies et al. |
| 7,439,393 B2 | 10/2008 | Box et al. |
| 7,488,827 B2 | 2/2009 | Laine et al. |
| 7,498,440 B2 | 3/2009 | Laine et al. |
| 7,501,011 B2 | 3/2009 | Powers et al. |
| 7,549,272 B2 | 6/2009 | DeFedericis |
| 7,629,335 B2 | 12/2009 | Biggadike et al. |
| 7,776,895 B2 | 8/2010 | Box et al. |
| 7,982,067 B2 | 7/2011 | Box et al. |
| 8,183,257 B2 | 5/2012 | Laine et al. |
| 8,303,991 B2 | 11/2012 | Staniforth |
| 8,309,572 B2 | 11/2012 | Laine et al. |
| 8,511,304 B2 | 8/2013 | Anderson et al. |
| RE44,874 E | 4/2014 | Box et al. |
| 9,365,905 B2 | 6/2016 | Newman et al. |
| 9,750,726 B2 | 9/2017 | Baker et al. |
| 2003/0026766 A1 | 2/2003 | Sanders |
| 2005/0121027 A1 | 6/2005 | Nilsson et al. |
| 2005/0124644 A1 | 6/2005 | Nilsson et al. |
| 2006/0134007 A1 | 6/2006 | Krueger et al. |
| 2006/0144733 A1 | 7/2006 | Wu et al. |
| 2006/0239932 A1 | 10/2006 | Monteith et al. |
| 2006/0239933 A1 | 10/2006 | Nilsson et al. |
| 2006/0257327 A1 | 11/2006 | Zierenberg et al. |
| 2006/0269708 A1 | 11/2006 | Merical et al. |
| 2007/0104655 A1 | 5/2007 | Zierenberg et al. |
| 2007/0110678 A1 | 5/2007 | Zierenberg et al. |
| 2007/0164254 A1 | 7/2007 | Powers |
| 2007/0212422 A1 | 9/2007 | Keller et al. |
| 2008/0003290 A1 | 1/2008 | Box et al. |
| 2008/0063719 A1 | 3/2008 | Morton et al. |
| 2009/0013998 A1 | 1/2009 | Nilsson et al. |
| 2009/0029901 A1 | 1/2009 | Wood-Kaczmar et al. |
| 2009/0041682 A1 | 2/2009 | Nilsson et al. |
| 2009/0152155 A1 | 6/2009 | Pasbrig |
| 2009/0188495 A1 | 7/2009 | Nilsson et al. |
| 2009/0192185 A1 | 7/2009 | Nilsson et al. |
| 2009/0234929 A1 | 9/2009 | Matsumoto |
| 2009/0298742 A1 | 12/2009 | Roche et al. |
| 2011/0017615 A1 | 1/2011 | Logel et al. |
| 2011/0269970 A1 | 11/2011 | Box et al. |
| 2012/0309725 A1 | 12/2012 | Baker et al. |
| 2014/0113888 A1 | 4/2014 | Crater |
| 2015/0313841 A1 | 11/2015 | Jones |
| 2016/0095840 A1 | 4/2016 | Baker et al. |

FOREIGN PATENT DOCUMENTS

| | | |
|---|---|---|
| EP | 239798 B1 | 9/1990 |
| EP | 466068 A2 | 1/1992 |
| EP | 0328685 B1 | 5/1992 |
| EP | 0606486 A4 | 10/1996 |
| EP | 0824480 A1 | 2/1998 |
| EP | 0606486 B1 | 8/2001 |
| EP | 1232745 B1 | 8/2002 |
| EP | 1240261 A1 | 9/2002 |
| EP | 1241110 A1 | 9/2002 |
| EP | 1243524 A2 | 9/2002 |
| EP | 1131059 B1 | 3/2003 |
| EP | 1691783 A1 | 8/2006 |
| EP | 1292510 B1 | 2/2007 |
| EP | 1232745 | 3/2007 |
| EP | 1232745 B1 | 3/2007 |
| EP | 1883400 B1 | 10/2008 |
| EP | 1990052 A1 | 11/2008 |
| EP | 1827283 A1 | 2/2009 |
| EP | 1991292 A1 | 12/2009 |
| EP | 2127628 A1 | 12/2009 |
| EP | 1626913 B1 | 2/2010 |
| EP | 2277799 A1 | 1/2011 |
| EP | 2283817 | 2/2011 |
| EP | 2283817 A1 | 2/2011 |
| EP | 2283818 | 2/2011 |
| EP | 2283818 A1 | 2/2011 |
| EP | 2954888 A1 | 12/2015 |
| FR | 2660634 A1 | 10/1991 |
| GB | 124009 | 3/1919 |
| GB | 124010 | 3/1919 |
| GB | 1242211 | 8/1971 |
| GB | 1381872 | 1/1975 |
| GB | 1424432 | 2/1976 |
| GB | 2064336 A | 6/1981 |
| GB | 2129691 A | 5/1984 |
| GB | 2169265 A | 7/1986 |
| GB | 2178965 A | 2/1987 |
| GB | 2242134 A | 9/1991 |
| GB | 2269992 | 3/1994 |
| GB | 2269992 A | 3/1994 |
| GB | 2410192 A | 7/2005 |
| JP | 2002532216 A | 10/2002 |
| WO | 1987/05213 | 9/1987 |
| WO | 1993/11746 | 6/1993 |
| WO | 1995/00128 | 1/1995 |
| WO | 1995/11666 | 5/1995 |
| WO | 1995032752 A1 | 12/1995 |
| WO | 1996/19199 | 6/1996 |
| WO | 1996/23485 | 8/1996 |
| WO | 1997/03649 | 2/1997 |
| WO | 1999/38493 | 8/1999 |
| WO | 1999040031 A2 | 8/1999 |
| WO | 1999/53901 | 10/1999 |
| WO | 2000/27363 | 5/2000 |
| WO | 2000/28979 | 5/2000 |
| WO | 2000/33811 | 6/2000 |
| WO | 2000037336 A1 | 6/2000 |
| WO | 2000/53157 | 9/2000 |
| WO | 2000/53158 | 9/2000 |
| WO | 2001/76575 | 10/2001 |
| WO | 2001/78694 | 10/2001 |
| WO | 2001087731 A2 | 11/2001 |
| WO | 2001097888 A2 | 12/2001 |
| WO | 2001098174 A1 | 12/2001 |
| WO | WO2002/12265 | 2/2002 |
| WO | WO 2002/12266 | 2/2002 |
| WO | 2002/43700 | 6/2002 |
| WO | 2002098874 A2 | 12/2002 |
| WO | 2003024439 A1 | 3/2003 |
| WO | 2003057593 A1 | 7/2003 |
| WO | 2003061743 A1 | 7/2003 |
| WO | 2004000541 A1 | 12/2003 |
| WO | 2004080808 A2 | 9/2004 |
| WO | 2004101390 A1 | 11/2004 |
| WO | 2004105727 A2 | 12/2004 |
| WO | 2004110404 A1 | 12/2004 |
| WO | 2005/004845 A1 | 1/2005 |
| WO | 2005004853 A1 | 1/2005 |
| WO | WO2005/004848 | 1/2005 |
| WO | 2005037280 A1 | 4/2005 |
| WO | 2005040304 A1 | 5/2005 |
| WO | 2005044186 A2 | 5/2005 |
| WO | 2005046636 A1 | 5/2005 |
| WO | 2005053644 A1 | 6/2005 |
| WO | 2005053645 A1 | 6/2005 |
| WO | 2005053646 A1 | 6/2005 |
| WO | 2005053647 A1 | 6/2005 |
| WO | 2005053648 A1 | 6/2005 |
| WO | 2005104745 A2 | 11/2005 |
| WO | 2005115462 A1 | 12/2005 |
| WO | 2005115463 A1 | 12/2005 |
| WO | 2005115464 A1 | 12/2005 |
| WO | 2005115465 A1 | 12/2005 |
| WO | 2005115466 A1 | 12/2005 |
| WO | 2005115467 A1 | 12/2005 |
| WO | 2005123002 A1 | 12/2005 |
| WO | 2006/008173 A2 | 1/2006 |
| WO | 2006000758 A1 | 1/2006 |
| WO | WO 2006/023457 A1 | 3/2006 |

(56) References Cited

FOREIGN PATENT DOCUMENTS

| | | |
|---|---|---|
| WO | 2006045715 A1 | 5/2006 |
| WO | 2006062883 A2 | 6/2006 |
| WO | 2006062931 A2 | 6/2006 |
| WO | 2006071844 A2 | 7/2006 |
| WO | 2006/108572 A2 | 10/2006 |
| WO | 2006/124556 A2 | 11/2006 |
| WO | 2006115264 A1 | 11/2006 |
| WO | 2006135474 A1 | 12/2006 |
| WO | 2007012871 A1 | 2/2007 |
| WO | 2007037748 A1 | 4/2007 |
| WO | 2007042822 A2 | 4/2007 |
| WO | 2007045378 A2 | 4/2007 |
| WO | 2007057081 A1 | 5/2007 |
| WO | 2007068896 A1 | 6/2007 |
| WO | 2007097451 A1 | 8/2007 |
| WO | 2007102635 A1 | 9/2007 |
| WO | 2007109606 A2 | 9/2007 |
| WO | WO2007/109698 | 9/2007 |
| WO | 2007/117911 | 10/2007 |
| WO | 2007109824 A1 | 10/2007 |
| WO | 2007121259 A2 | 10/2007 |
| WO | 2007/135024 A1 | 11/2007 |
| WO | 2008012338 A2 | 1/2008 |
| WO | 2008014862 A1 | 2/2008 |
| WO | 2008021142 A2 | 2/2008 |
| WO | 2008040841 A1 | 4/2008 |
| WO | 2008/049842 A2 | 5/2008 |
| WO | 2008091968 A1 | 7/2008 |
| WO | 2008121321 A1 | 10/2008 |
| WO | 2008135570 A1 | 11/2008 |
| WO | 2009013243 A1 | 1/2009 |
| WO | 2009013244 A1 | 1/2009 |
| WO | 2009029029 A1 | 3/2009 |
| WO | 2009036243 A1 | 3/2009 |
| WO | 2009/090010 A1 | 7/2009 |
| WO | 2009103336 A1 | 8/2009 |
| WO | 2009155387 A2 | 12/2009 |
| WO | 2010038086 A2 | 4/2010 |
| WO | 2010072354 A1 | 7/2010 |
| WO | 2010097114 A1 | 9/2010 |
| WO | 2010097115 A1 | 9/2010 |
| WO | 2010135340 A2 | 11/2010 |
| WO | 2011067212 A1 | 6/2011 |
| WO | 2012168160 A1 | 12/2012 |
| WO | 2012168161 A1 | 12/2012 |

OTHER PUBLICATIONS

Allen et al., Fluticasone Furoate (FF) A Novel Inhaled Corticosteroid (ICS) Demonstrates Prolonged Lung Absorption Kinetics in Man. American Thoracic Society 2010 International Conference, Abstract D21 Asthma Therapy: New Targets, New Tricks. DOI: http://dx.doi.org/10.1164/ajrccm-conference.2010.181.1_MeetingAbstracts.A5408 (2010).
Allen et al., Fluticasone furoate, a novel inhaled corticosteroid, demonstrates prolonged lung absorption kinetics in man compared with inhaled fluticasone propionate. Clin Pharmacokinet. Jan. 2013;52(1):37-42.
Barnes, Triple inhalers for obstructive airways disease: will they be useful? Expert Rev Respir Med. Jun. 2011;5 (3):297-300.
Biggadike, Fluticasone furoate/fluticasone propionate—different drugs with different properties. Clin Respir J. Jul. 2011;5(3):183-4.
Cazzola et al., The scientific rationale for combining long-acting beta2-agonists and muscarinic antagonists in COPD. Pulm Pharmacol Ther. Aug. 2010;23(4):257-67.
Donohue et al., A randomized, double-blind dose-ranging study of the novel LAMA GSK573719 in patients with COPD. Respir Med. Jul. 2012;106(7):970-9.
Donohue et al., Efficacy and safety of once-daily umeclidinium/vilanterol 62.5/25 mcg in COPD. Respir Med. Oct. 2013;107(10):1538-46.
Donohue et al., Magnitude of umeclidinium/vilanterol lung function effect depends on monotherapy responses: Results from two randomised controlled trials. Respir Med. Mar. 2016;112:65-74.
Eklira Genuair 322 micrograms inhalation powder, Summary of Product Characteristics.
FDA, U.S. Food & Drug Administration, TUDORZA™ PRESSAIR™—US FDA Approved Product Label. Retrieved online at: http://www.accessdata.fda.gov/scripts/cder/daf/index.cfm?event=BasicSearch.process (2012).
Fluticasone, www.Drugs.com, Wolters Kluwer Health (Wayback) (Jun. 4, 2009).
Forest Pharmaceuticals, Highlights of Prescribing Information, Tudorza Pressair. (2012).
GlaxoSmithKline, Evaluate the Safety, Efficacy and Dose Response of GSK573719 in Combination With Fluticasone Furoate in Subjects With Asthma (ILA115938). ClinicalTrials.gov Identifier NCT01573624, First Received Apr. 5, 2012, retrieved online at: https://clinicaltrials.gov/ct2/show/NCT01573624.
GlaxoSmithKline, Highlights of Prescribing Information, Anoro Ellipta, FDA NDA 203975s003. (2016).
GSK Annual Report, retrieved online at: http://annualreport.gsk.com/ (2015).
Jones, Aclidinium bromide twice daily for the treatment of chronic obstructive pulmonary disease: a review. Adv Ther. Apr. 2013;30(4):354-68.
Laine et al., Discovery of novel 1-azoniabicyclo[2.2.2]octane muscarinic acetylcholine receptor antagonists. J Med Chem. Apr. 23, 2009;52(8):2493-505.
Laine et al., The pre-clinical pharmacology of the inhaled muscarinic antagonist GSK573719 predicts once-daily clinical dosing. European Respiratory Journal, 2011; 38(Suppl 55):3450.
Peters et al., Tiotropium bromide step-up therapy for adults with uncontrolled asthma. N Engl J Med. Oct. 28, 2010;363(18):1715-26.
Rosebraugh, Center for Drug Evaluation and Research, Approval Package for: Application No. 203975. Dec. 18, 2013.
Schelfhout et al., Activity of aclidinium bromide, a new long-acting muscarinic antagonist: a phase I study. Br J Clin Pharmacol. May 2010;69(5):458-64.
Welte et al., Efficacy and tolerability of budesonide/formoterol added to tiotropium in patients with chronic obstructive pulmonary disease. Am J Respir Crit Care Med. Oct. 15, 2009;180(8):741-50.
World Health Organization, The top 10 causes of death. WHO Fact Sheet No. 310, retrieved online at: http://www.who.int/mediacentre/factsheets/fs310/en/, Updated May 2014.
Response filed Apr. 14, 2015 to U.S. Office Action for U.S. Appl. No. 13/510,962, dated Jan. 14, 2015.
Response filed Apr. 15, 2016 to U.S. Office Action for U.S. Appl. No. 14/651,988, dated Feb. 25, 2016.
Response filed Aug. 20, 2014 to U.S. Office Action for U.S. Appl. No. 13/510,962, dated Jun. 20, 2014.
Response filed Jun. 21, 2013 to U.S. Office Action for U.S. Appl. No. 13/510,962, dated Jun. 10, 2013.
Response filed Mar. 10, 2014 to U.S. Office Action for U.S. Appl. No. 13/510,962, dated Oct. 9, 2013.
Response filed May 2, 2016 to U.S. Office Action for U.S. Appl. No. 14/124,276, dated Feb. 2, 2016.
Response filed Sep. 23, 2016 to U.S. Office Action for U.S. Appl. No. 14/651,988 dated Jun. 23, 2016.
U.S. Notice of Allowance for U.S. Appl. No. 14/651,988, dated Nov. 16, 2016.
U.S. Office Action for U.S. Appl. No. 13/510,962, dated Jan. 14, 2015.
U.S. Office Action for U.S. Appl. No. 13/510,962, dated Jun. 10, 2013.
U.S. Office Action for U.S. Appl. No. 13/510,962, dated Jun. 16, 2015.
U.S. Office Action for U.S. Appl. No. 13/510,962, dated Jun. 20, 2014.
U.S. Office Action for U.S. Appl. No. 13/510,962, dated Oct. 9, 2013.
U.S. Office Action for U.S. Appl. No. 14/124,276, dated Feb. 2, 2016.

(56) References Cited

OTHER PUBLICATIONS

U.S. Office Action for U.S. Appl. No. 14/124,276, dated Jul. 6, 2016.
U.S. Office Action for U.S. Appl. No. 14/651,988 dated Jun. 23, 2016.
U.S. Office Action for U.S. Appl. No. 14/651,988, dated Feb. 25, 2016.
U.S. Appl. No. 12/353,436, filed Jan. 14, 2009, Muscarinic Acetylcholine Receptor Antagonists.
U.S. Appl. No. 13/401,890, filed Feb. 22, 2012, Muscarinic Acetylcholine Receptor Antagonists.
U.S. Appl. No. 13/510,962, filed Aug. 20, 2012, Combinations of a Muscarinic Receptor Antagonist and a Beta-2 Adrenoreceptor Agonist.
U.S. Appl. No. 14/651,988, filed Jun. 12, 2015, Combination of Umeclidinium, Fluticasone Propionate and Salmeterol Xinafoate for Use in the Treatment of Inflammatory or Respiratory Tract Diseases.
ADVAIR DISKUS® Presecribing Infiormation Aug. 2003.
ADVAIR HFA® Prescribing Information Jun. 2006.
Ahmed, Ph D Thesis "Particle Interactions in Multicomponent Systems" 1989.
Anonymous, "View of NCT01673624 on Apr. 6, 2012" ClinicalTrials. gov; 2012: pp. 1-4.
Agusti, et al "A comparison of the efficacy and sefety of once-daily fluticasone furoate/valanterol with twice daily fluticasone propionate / salmeterol in moderate to very severe COPD" Eur Respir J; 2014; vol. 43; pp. 763-772.
Aulton, Michael E., "Pharmaceutics: the science of dosage form design." 1998; pp. 584-590.
Barnes P.J., BMJ vol. 333, Jul. 29, 2006, pp. 246-248.
Barnes P.J., et. al., Chest 2000, 117, 63S-66S.
Bateman et al, "Efficacy and safety of the long-acting muscarinic antagonist GSK233705 delivered once daily in patients with COPD", The Clinical Respiratory Journal, pp. 248-257, 2012.
Bossert, et al, "Effect of Mixing on the Lubrication of Crystalline Lactose by Magnesium Stearate" 1980; Drug Development and industrial Pharmacy; vol. 6(6); pp. 573-589.
BREO Ellipta Presecribing information May 2017 pp. 1-58.
Busse, et al., "Expert Panel Report 3 (EPR-3): Guidelines for the Dignosis and Management of Asthma—Summary Report 2007" Allergy, Asthma & Immun=ology; 2007; pp. S94-S138; vol. 120, No. 5.
Casarosa et al, "Preclinical Evaluation of Long-Acting Muscarinic Antagonists: Comparison of Tiotropium and Investigational Drugs", The Journal of Pharmacology and Experimental Therapeutics, vol. 330, No. 2, pp. 660-668, 2009.
Caverly et al, "Fluticasone furoate, vilanterol and lung function decline in patients with moderate COPD and heightened cardiovascular risk", AJRCCM, vol. 197: 47, 2018.
Cazzola and M.G. Matera, Novel long-acting bronchodilators or COPD and asthma; British Journal of Pharmacology 155.3 (2008): 291-299.
Cazzola, and M. G. Matera, Emerging inhaled bronchodilators: an update. European Respiratory Journal 34.3 (2009): 757-769.
Cazzola et al., Drug Discovery Today: Therapeutic Strategies vol. 3, No. 3 2006, pp. 277-286.
Cazzola, "Aclidinium bromide, a novel long-acting muscarinic M3 antagonist for the treatment of COPD", Current Opinion in Investigational Drugs, 2009, 10(5), pp. 482-490.
Cazzola, Current opinion: Pharmacological approaches in asthma and COPD; Breathe 6.1 (2009): 24-35.
Covelli et al, "Efficacy and safetty of fluticasone furoate/vilanterol or tiotropium in subjects with COPD at cardiovascular risk" International J of COPD, (2016); 11, pp. 1-12.
Clinical Study NCT00976144—Safety, Tolerability, Pharmacokinetic and Pharmacodynamic Effects of GSK573719 (LAMA) and GW642444 (LABA) Administered Individually and Concurrently in Healthy Japanese Subjects (DB2113208); Healthy Japanese Subjects (DB2113208).

Dransfield et al Once-Daily inhaled Fluticasone furoate and vilanterol vs vilanterol only for prevention of exacerbations of COPD: two replicate double blind paralel group randomized controlled trials, www.thelancet.com/respiratory, vol. 1, May 2003, pp. 210-223.
Dransfield et al , "Efficacy and safety of once-daily fluticasone furoate/vilanterol (100/25 mcg) vs twice-daily fluticasone propionate / salmeterol (250/50 mcg) in COPD patients" Respiratory Medicine; 2014; pp. 1171-1179; vol. 108.
Cazzola, Expert Opin. Investig. Drugs (2005) 14(7):775-783.
Fee, et al, "influence of hydrophobic materials on dissolution of a nondisintegrating hydrophilic solid (potassium chloride)" J PharmSci; 1976 pp. 182-187; vol. 65.
Ganderton, The generation of Resopirable clouds from Coarse Powder Aggregates 1992; J of Biopharmaceutical Sciences; vol. 3 (1/2); pp. 101-105.
Global Initiative for Chronic Obstructive Lung Disease (GOLD) "The global strategy for the diagnosis, management, and prevention of chronic obstructive pulmonary disease" 2009 Medical Communications Resources Inc.
Global Initiative for Asthma (GINA) "The global strategy for asthma management and prevention" 2009 Medical Communications Resources Inc.
Global Initiative for the Diagnosis, Management and Prevention of Chronic Obstructive Pulonary Disease, p. 14 (2016).
Gross N.J., Anticholinergic agents in asthma and COPD; European Journal of Pharmacology 533.1-3 (2006): 36-39.
Gupta A. et al., Difference in the lubrication efficiency of bovine and vegetable-derived magnesium stearate during tabletting; AAPS PharmSciTech 10.2 (2009): 500-504.
FDA.gov details of ANORO ELLIPTA approved Dec. 18, 2013.
ANORO® Summary of product characteristics (SmPC) European Medicines Agency.
Joos G. et. al., British Journal of Clinical Pharmacology 2010, 69, 458-464.
FDA NDA 203975 Approval Letter Dec. 18, 2013.
Hanania, et al "the Efficacy and Safety of the Novel Long-Acting B2 Agonist Vilanterol in pateinets with COPD" 01; Jul. 2012; Chest; vol. 142; pp. 119-127.
Jones et al., Efficacy and safety of once-daily aclidinium in chronic obstructive pulmonary disease, Respiratory Research (2011), 12:55 http://respiratory-research.com/content/12/1/55.
Kassem, Ph D "Generation of Deeply Inspirable Clouds from Dry powder Mixtures" 1990.
Kawashima, et al. Design of Ihalation dry powder of pranlukast hydrate to improve dispersibility by the surface bmodification with light anhydrous silicic acid )Aerosil 200); Intl J of Pharmaceutics; 1998; pp. 243-251; vol. 173.
Kerwin, et al. "A randomized trial of fluticasone furoate/vilanterol (50/25 mcg; 100/25 mcg) on lung function in COPD", Respiratory Medicine, (2013)107, 560-569.
Laine et al, "Design, Synthesis, and Structure—Activity Relationship of Tropane Muscarinic Acetylcholine Receptor Antagonists", Journal of Medicinal Chemistry, vol. 52, pp. 5241-5252, 2009.
Meakin, et al "the Effect of Flow rate on Drug Delivery from the Pulivinal, a High Resistance Dry Powder Inhaler" 1998; J. of Aerosol Medicine ; vol. 11(3); pp. 143-152.
Naito, et al, "Applications of Comminution Techniques for the surface Modificaion of Powder Meterials" ISIJ International ; 1993; pp. 915-924; vol. 33(9).
Staniforth, et al., "Interparticle forces in binary and ternary ordered powder mixes." J. Pharm. Pharmacol.; 1982; 141-145; vol. 34.
Decision of Technical Board of Appeal Mar. 3, 2002 T484/09.
U.S. Appl. No. 14/970,945, filed Dec. 16, 2015: file history.
Prat et al, "Discovery of Novel Quaternary Ammonium Derivatives of (3R)-Quinuclidinol Esters as Potent and Long-Acting Muscarinic Antagonists with Potential for Minimal Systemic Exposure after Inhaled Administration: Identification of (3R)-3-{[Hydroxy(di-2-thienyl)acetyl]oxy}-1-(3-phenoxypropyl)-1-azoniabicyclo[2.2.2]octane Bromide (Aclidinium Bromide)", Journal of Medicinal Chemistry, vol. 52, pp. 5076-5092, 2009.

(56) References Cited

OTHER PUBLICATIONS

FDA Pulmonary Allergy Drugs Advisory Committee Meeting, Feb. 23, 2012, NDA 20-2450: aclidinium bromide for the long-term, maintenance treatment of bronchospasm associated with chronic obstructive pulmonary disease (COPD), including chronic bronchitis and emphysema. (UMC292620). Retrieved from: https://www.fda.gov/downloads/AdvisoryCommittees/CommitteesMeetingMaterials/Drugs/Pulmonary-AllergyDrugsAdvisoryCommittee/UCM292620.pdf.
Martinez, et al., "Fluticasone furoate /vilanterol (100/25; 200/25 mcg) improves lung function in COPD: a randomized trial", Respiratory Medicine, (2013), 107 pp. 550-559.
Martinez, et al., "Effect of Fluticasone furoate /vilanterol or tiotropium on Exacerbations of Chronic Obstructive Pulmonary Disease in Patients with Moderate Airflow Obstruction" Am J Respir Crit Care Med., vol. 195, issue 7, pp. 881-888, Apr. 1, 2017.
Opposition (EP2506844)—Sima Patent Lisanslama Hizmettier Ltd STI, Filed Sep. 20, 2018.
Opposition (EP2506844)—Dr. Markus Brewer, of Henkele Breuer & Partner, Filed Sep. 19, 2018.
Opposition (EP2506844)—Teva UK Limited, Filed Sep. 17, 2018.
Peart, et al "Multicompoennt Particle Interactions in Dry Powder Aerosols" Nov. 1997; Pharmaceutical Research; Supplement 142; vol. 14(11); para 1405.
Siler et al, A randomized, phase III trial of once-daily fluticasone/vilanterol 100/25 mcg vs once daily vilanterol 25 to evaluate the contribution oon lung function of fluticsone furoate in the combination in patients with COPD.: Respiratory Medicine, 123, (2017), pp. 8-17.
Vilanterol; National Center for Biotechnology Information, PubChem Compound Database; CID=10184665, https://pubchem.ncbi.nlm.nih.gov/compound/10184665.
G Villetti et al, "Bronchodilator Activity of (3R)-3-[[[(3-fluorophenyl)[3,4,5-trifluorophenyl)methyl]amino] carbonyl] oxy]-1-[2-oxo-2-(2-thienyl)ethyl]-1-azoniabicyclo[2.2.2] octane bromide (CHF5407), a Potent, Long-Acting, and Selective Muscarinic M3 Receptor Antagonist", The Journal of Pharmacology and Experimental Therapeutics, vol. 335, No. 3, pp. 622-635, 2010.
Who Drug Information, vol. 22, No. 2, 2008, p. 132.
Woodcock, et al., "Efficacy and Safety of Fluticasone Furoate/Vilanterol Compared with Fluticasone Proionate / Salmeterol Combination in Adult and Adoescent Patients with persistant Asthma" Chest; 2013; pp. 1222-1229; vol. 144, No. 4.
Zeng X.M. et al., "Particulate interactions in dry powder formulations for inhalation" Taylor & Francis, 2001, London, pp. 156-159.
Response filed Jun. 10, 2016 to U.S. Office Action for U.S. Appl. No. 14/970,945, dated Feb. 12, 2016.
Response filed Oct. 24, 2016 to U.S. Office Action for U.S. Appl. No. 14/970,945, dated Aug. 24, 2016.
U.S. Notice of Allowance for U.S. Appl. No. 14/970,945, dated Jan. 11, 2017.
U.S. Office Action for U.S. Appl. No. 14/970,945, dated Aug. 24, 2016.
U.S. Office Action for U.S. Appl. No. 14/970,945, dated Feb. 12, 2016.
U.S. Appl. No. 14/970,945, filed Dec. 16, 2015, Combinations of a Muscarinic Receptor Antagonist and a Beta-2 Adrenoreceptor Agonist.
EP1232745 Statement of Grounds for Appeal dated Mar. 25, 2010.
EP1232745 Decision of the Enlarged Board of Appeal in review procedure dated Jul. 30, 2012.
EP1232745 Written Decision in Preparation to/during Oral Proceedings dated Aug. 27, 2009, pp. 1-34.
EP1232745 Reply of Patent Proprieter to the Notice(s) of Opposition dated Oct. 9, 2008.
EP1232745 Reply of Patent Proprieter to the Notice(s) of Opposition dated Sep. 25, 2008.
EP1232745 Notice of Opposition dated Dec. 6, 2007.
EP1232745 Notice of Opposition dated Dec. 10, 2007.
EP1232745, Minutes of the Oral Proceedings (Opposition division), Oct. 27, 2009, pp. 1-10.
EP1232745,F3032 Notification of the Decision, pp. 1-23, May 18, 2011.
EP2283817, Notice of Opposition dated Feb. 16, 2017, pp. 1-21.
EP2283817, Reply of Patent Proprietor to Notice(s) of Opposition dated Aug. 10, 2017.
EP2283817, Brief Communication—Opposition Proceedings, Jul. 14, 2017, pp. 1-6.
EP2283817, Brief Communication—Opposition Proceedings, Aug. 28, 2018. pp. 1-164.
EP2283817, Written Submission in preparation to/during Oral Proceedings Aug. 23, 2010, pp. 1-31.
EP2400950—"Response to Communication dated Aug. 9, 2012" dated Feb. 14, 2013.
EP2400950—"Official Action" dated Aug. 9, 2012.
EP2400950—Marked Claims Feb. 2013.
EP2400950—Ummarked Claims Feb. 2013.
Shur, J. et al "From single excipients to dual excipient platforms in dry powder inhaled products." Inl J. of Pharmaceuticals; 2016; pp. 374; vol. 514.
The London Gazzette, "Medicines Control Agency—Licenses Granted" Feb. 23, 2001; [https://www.thegazette.co.uk/notice/L-5613-1003].
U.S. Appl. No. 13/819,149, filed Feb. 26, 2013.
U.S. Appl. No. 13/819,149 "Non-Final Rejection" dated Dec. 5, 2013.
U.S. Appl. No. 13/819,149 "Response after Non-Final Action" dated Feb. 26, 2014.
U.S. Appl. No. 13/819,149 "Final Rejection" dated Jun. 20, 2014.
U.S. Appl. No. 13/819,149 "Non-Final Rejection" dated Mar. 6, 2015.
U.S. Appl. No. 13/819,149 "Non-Final Rejection" dated Mar. 30, 2016.
U.S. Appl. No. 13/819,149 "Response after Non-Final Action" dated Jun. 28, 2016.
U.S. Appl. No. 13/819,149 "Final Rejection" dated Oct. 3, 2016.
U.S. Appl. No. 13/819,149 Non-Final Rejection dated Apr. 7, 2017.
U.S. Appl. No. 13/819,149 "Response after Non-Final Action" dated Jul. 6, 2017.
U.S. Appl. No. 13/819,149 "Final Rejection" dated Oct. 20, 2017.
U.S. Appl. No. 13/819,149 "Non-Final Rejection" "dated Aug. 27, 2018".
U.S. Appl. No. 13/819,149 "Response after Non-Final Action" dated Sep. 26, 2018.
U.S. Appl. No. 13/819,149 "Final Rejection Jan. 7, 2019".
U.S. Appl. No. 13/819,184, filed Feb. 26, 2013.
U.S. Appl. No. 13/819,184 Non-final Rejection dated Apr. 16, 2018.
U.S. Appl. No. 13/819,184 Applicant's Response to non-Final Rejection of Oct. 2, 2017 dated Dec. 11, 2017.
U.S. Appl. No. 13/819,184 Non-final Rejection dated Oct. 2, 2017.
Van Kamp, et al. "The Role of Water Uptake in Tablet Disiintegration" 1986; Pharm Acta Helv; vol. 61 (1); pp. 22-29.
Vestbo, et al. "Fluticasone furoate and vilanterol and survival in chronic obstructive pulmonary disease with heightened cardiovascular risk (SUMMIT); a double blind randomized controlled trial" www.thelancet.com, vol. 387, Apr. 30, 2016, pp. 1817-1826.
Vestbo, et al. "Effectiveness of Fluticasone furoate—Vilanterol for COPD in Clinical Practice" The New England Journal of Medicine; 2016; pp. 1253-1260; vol. 375.
Wade., A, et al., "Handbook of Pharmaceutical Excipients 2nd Edition" 1994; pp. 252-261; London: The Pharmaceutcal Press.
Ray, Nicholas. Alcaraz, Lilian. "Muscarinic antagonist-β-adrenergic agonist dual pharmacology molecules as bronchodilators: a patent review". Expert Opin. Ther. Patents (2009) 19 (1): 1-12 published May 1, 2009.
Westmeier et al., "Combination Particles Containing Salmeterol Xinafoate and Fluticasone Propionate: Formulation and Aerodynamic Assessment," Journal of Pharmaceutical Sciences, vol. 97, No. 6, Jun. 2008.
Letter of the USAN dated May 25, 2011 relating to umeclidinium.
Letter of the USAN dated May 25, 2011 relating to umeclidinium bromide.
Letter of the USAN dated Sep. 30, 2009 relating to vilanterol.

(56) References Cited

OTHER PUBLICATIONS

Letter of the USAN dated Sep. 30, 2009 relating to vilanterol trifenatate.
US Pharmacopeia, USP 31 vol. 1, pp. 605-607 as in force as of May 1, 2008.
Press release for ANORO US approval.
P. Kuna et al., "Once-daily dosing with budesonide/formoterol compared with twice-daily budesonide/formoterol and once-daily budesonide in adults with mild to moderate asthma", Respiratory Medicine (2006) 100, 2151-2159.
R. Kempsford et al., GW642444, a Novel Inhaled Long-acting Beta2 Adrenoceptor Agonist (LABA) at single doses of 25, 50 and 100 mcg, is well tolerated an demonstrates prolonged bronchodilation in COPD patients, Am. J. Respir. Crit. Care Med 181;2010:A4447.
EP2506844B1 GSK Response to Oppositions dated Apr. 29, 2019.
Umeclidinium Bromide; National Center for Biotechnology Information, PubChem Compound Database; CID=11519069, https://pubchem.ncbi.nlm.nih.gov/compound/11519069.
Sep. 6, 2019 Reply of the patent proprietor to Jun. 17, 2019 EP opponent 1 submission.
Patent Proprietor's Reply to Appeal, EP2611423, filed Feb. 6, 2019, pp. 1-18.
Physician's Desk Reference, Thompson Reuters, 63rd edition, 2009, pp. 1276-1288, 1435-1440 and 1594-1601.
Possumato, Adrian. "New Pharmaceutical Application Demad Intelligent Sorbents: Novel Formualtions and Drug-Delivery Systems Require Optimized Packaging Protection" Oct. 2007; pp. 1-5.
Regulatory Dossier for Relvar Ellipta, pp. 1-6, cited in opposition of EP2611423, Feb. 19, 2018.
Relvar Ellipta device (patentee's submission of Feb. 19, 2018, cited in opposition of EP2611423).
Relvar Ellipta Package Leaflet; Jan. 2, 2019.
Reply of the Patent Proprietor to the Notice of Opposition for EP2611423, dated Dec. 6, 2016, pp. 1-49.
U.S. Appl. No. 13/510,962, filed Aug. 20, 2012.
U.S. Appl. No. 13/819,149, Applicant's response to Office Action of Mar. 6, 2015, dated Jun. 3, 2015.
U.S. Appl. No. 13/819,149, Final Office Action dated Aug. 27, 2015.
U.S. Appl. No. 13/819,149, Request for Continued Examination dated Nov. 23, 2015.
U.S. Appl. No. 13/819,149, Request for Continued Examination dated Sep. 17, 2014.
U.S. Appl. No. 13/819,149, Response to Restriction Requirement dated Oct. 21, 2013.
U.S. Appl. No. 13/819,149, Restriction Requirement dated Sep. 26, 2013.
U.S. Appl. No. 13/819,149, Claims and Applicants Arguments/Remarks Made in Admentment, filed Apr. 5, 2019.
U.S. Appl. No. 13/819,149, Non-Final Rejection, dated Jun. 27, 2019.
U.S. Appl. No. 14/124,276, Office Action dated Feb. 2, 2016.
U.S. Appl. No. 14/124,276, Office Action dated Jul. 6, 2016.
U.S. Appl. No. 14/651,988, filed Jun 12, 2015.
U.S. Appl. No. 14/970,945, Notice of Allowance, dated Apr. 20, 2017.
U.S. Appl. No. 14/970,945, Request for Continued Examination, dated Nov. 23, 2016.
U.S. Appl. No. 14/970,945, Request for Contd Examination including Arguments/Remarks and Claims, dated Apr. 11, 2017.
U.S. Appl. No. 15/678,246, filed Aug. 16, 2017
U.S. Appl. No. 15/678,246, Non-Final Rejection dated Sep. 5, 2018.
U.S. Appl. No. 15/678,246, Requirement for Restriction, dated Dec. 1, 2017.
U.S. Appl. No. 15/678,246, Response to Restriction dated Feb. 1, 2018.
U.S. Appl. No. 13/819,184, Amendment filed dated Feb. 3, 2015.
U.S. Appl. No. 13/819,184, Final Rejection dated Nov. 7, 2014.
U.S. Appl. No. 13/819,184, Non-Final Office Action dated Sep. 24, 2013.
U.S. Appl. No. 13/819,184, Non-Final Rejection dated May 1, 2014.
U.S. Appl. No. 13/819,184, Response to Non-Final Rejection dated Jul. 17, 2014.
U.S. Appl. No. 13/819,184, Response to Office Action dated Dec. 17, 2013.
Statement of Grounds of Appeal, EP2611423, Sep. 26, 2018, Teva, pp. 1-15.
Statement of Grounds of Appeal, EP2611423, Sep. 27, 2018, Dr. Andreas Oser, pp. 1-25.
Statement of Grounds of Appeal, EP2611423, Sep. 27, 2018, Generics UK, pp. 1-15.
Sterling, et al., "Dose-Related Efficacy and Optimal Once-Daily (od) Dosing Interval of the Long-Acting Beta2 Agonist(laba), Vilanterol Trifenatate (vi), In Adults With Persistent Asthma" Am J Respir Crit Care Med, May, 17, 2011; C39 Novel Therapeutic Options in Airways Disease; Thematic Poster Session.
Submissions of the Proprietor in the examination proceedings related to the opposed Eur. Pat. Appl. 09 889096.8-1219 dated Feb. 4, 2013; Response to Aug. 9, 2012 Communication.
T 0805/93 (OP3's submission of Jan. 18, 2018), opposition of EP2611423.
Telko, et aL, "Dry Powder Inhaler Formulation" Respiratory Care; 2005; vol. 50, No. 9; pp. 1209-1227.
To, Masako, et al., "Fluticasone Furoate, A Novel Enhanced-affinity Inhaled Corticosteroid (ICS), Has More Potent Anti-inflammatory Effects Than Fluticasone Propionate in Peripheral Blood Mononuclear Cells From Asthma and COPD Patients", Am J RespirCrit Care Med; 2010; vol. 181.
Vaczek, "Dialing in stable packaging for sensitive drugs" Pharmaceutical and Medical Packaging News; 2010.
View of NCT01128569 on Jun. 4, 2010. ClinicalTrials.gov archive [online], Jun. 4, 2010, [search at Apr. 30, 2014], URL,.
View of NCT01134042 on Jul. 16, 2010. ClinicalTrials.gov archive [online], Jul. 16, 2010, [search at Apr. 30, 2014], URL,.
Web Page of GSK Clinical Trial 1128569, dated May 20, 2010.
Wetterlim; "Turbuhaler: A New Powder Inhaler for Administration of Drugs to the Airways"; Pharm. Res.; 1988; vol. 5 (8); pp. 506-508.
Williams, R.O., III, et al., "Investigation of moisture scavengers in pressurized metered-dose inhalers," 2000:S.T.P. Pharma Sciences; vol. 10(3); pp. 243-250 (Abstract).
World Health Organization, WHO Technical Report Series, No. 953, 2009, Annex 2: Stability testing of active pharmaceutical ingredients and finished pharmaceutical products.
Written Submission in preparation to/during oral proceedings, EP2611413, Jan. 8, 2018, Dr. Andreas Oser, pp. 1-12.
Written Submission in preparation to/during oral proceedings, EP2611423, Jan. 8, 2018, Teva, pp. 1-15.
Young, et al., "Influence of Humidity on the Electrostatic Charge and Aerosol Performance of Dry Powder Inhaler Barrier Based Systems." Pharmaceutical Research; May 2007; vol. 24, No. 5; pp. 963-970.
OPP D48—N. Islam, P. Stewart, I. Larson and P. Hartley „Effect of Carrier Size on the Dispersion of Salmeterol Xinafoate from Interactive Mixtures Journal of Pharmaceutical Sciences Apr. 2004, 93, 1030-1038.
OPP D49—V. N. P. Le, T. H. Hoang hi, E. Robins and M. P. Flament, AAPS PharmSciTech Jun. 2012, 13, 477-484.
OPP D50—B. Mei Jin Tanm L. Wah Chan and P. Wan Sia Heng, „Chapter 11 Milling and Blending: Producing the Right Particles and Blend Characteristics for Dry Powder Inhalation Pharmaceutical Inhalation Aerosol Technology Third Edition 2019, p. 273-284.
OPP D51—J. Shur, H. Harris, M.D. Jones, J.S. Kaeger and R. Price „The Role of Fines in the Modification of the Fluidization and Dispersion Mechanism Within Dry Powder Inhaler Formulations Pharmaceutical Research Jul. 2008, 25, 1931-1940.
OPP D52—M. J. Telko and A. J. Hickey "Dry Powder Inhaler Formulation" Respiratory Care Sep. 2005, 50, 1209-1227 Listed on Helios Prepared SB08 4 of 4.
OPP D53—S. J. Charlton "Agonist efficacy and receptor desensitization: from partial truths to a fuller picture" British Journal of Pharmacology 2009, 158, 165-168.
OPP D55—print-out from https://clinicaltrials.gov/ct2/show/NCT01147848, version dated Jan. 18, 2017.

(56) References Cited

OTHER PUBLICATIONS

OPP D56—print-out from https://clinicaltrials.gov/ct2/show/NCT0606684, version dated Feb. 1, 2008.
OPP D57—print-out from https://clinicaltrials.gov/ct2/show/NCT00606684, version dated Dec. 16, 2016.
OPP D58—print-out from https://www.gsk-studyregister.com/study?uniqueStudyId=B2C111045 Mar. 9, 2020.
OPP D59—print-out from https://clinicaltrials.gov/ct2/show/NCT01147848, version dated Jan. 22, 2009.
OPP D60—print-out from https://clinicaltrials.gov/ct2/show/NCT00600171, version dated Dec. 16, 2016.
OPP D61—print-out from https://www.gsk-studyregister.com/study?uniqueStudyId=B2C109575 Mar. 9, 2020.
OPP D62—print-out from https://clinicaltrials.gov/ct2/show/NCT00731822, version dated Aug. 8, 2008.
OPP D63—print-out from https://clinicaltrials.gov/ct2/show/NCT00731822, version dated Dec. 8, 2016.
OPP D64—print-out from https://www.gsk-studyregister.com/study?uniqueStudyId=HZC111348 Mar. 9, 2020.
OPP D65—print-out from https://pipelinereview.com/index.php/2008122224291/Small-Molecules/GS Kand-Theravance-an nou nce-positive-phase release dated Dec. 22, 2008.
OPP D66—print-out from http://investor.inva.com/news-releases/news-release-details/th eravance- reportsfourth-quater-and-full-year-2008-results, press release dated Feb. 12, 2009.
OPP D67—B. Beilmann, R. Kubiak, P. Grab, H. Hausler and P. Langguth 11Effect of Interactive Ternary Mixtures on Dispersion Characteristics of Ipratropium Bromide in Dry Powder Inhaler Formulations AAPS PharmSciTTech 2007 Apr. 20, 2007, 8, E1-E8.
OPP D68—S. Lawrence Lee, W. P. Adams, B. V. Li, D. P. Connr, B. A. Chowdhurry and L. X. Yu „In Vitro Considerations to Support Bioequivalences of Locally Actinng Drugs in Dry Powder Inhalers for Lung Diseases The AAps Journal Sep. 3, 2009, 11, 414-423.
OPP D71—print out from https ://www.ema.europe.eu/en/documents/scientific-guideline/note- guidanceclinical-investigation-medicinal-products-treatments-asthma_en.pdf, press release from Nov. 21, 2002.
OPP D72—print out from Belgian medicinal product register 2008 (Repertoire Commente Des Medicaments 2008).
OPP D75—Global Initiative for Chronic Obstructive Lung Disease (GOLD),"Global Strategy for the diagnosis management, and prevention of chronic obstructive pulmonary diisease" 2006, MCR Vision, Inc.
OPP D76—Global Initiative for Asthma (GINA), "Global Strategy for Asthma Management and Prevention" 2008 (update).
OPP D77—M. Cazzola et al., Ultra long acting j32-agonists in development for asthma and chronic obstructive pulmonary disease, Expert Opin. Investig. Drugs (2005) 14(7), pp. 775-783.
OPP D79—M. G. Matera et al., Ultra-long-acting j32-adrenoceptor agonists—an emerging therapeutic option for asthma and COPD?, Drugs 2007; 67(4), pp. 503-515.
OPP D82—USAN information vilanterol and vilanterol trifenatate (downloaded on Feb. 13, 2020).
OPP D83—USAN information fluticasone furoate (downloaded on Feb 13, 2020).
OPP D84—R. Kempsford at al.; The pharmacodynamics, pharmacokinetics and tolerability of repeat doses of the novel inhaled long-acting beta2 adrenoceptor agonist (LABA) GW642444 (25, 50 and 100 mcg) in healthy subjects; Am J Respir Crit Care Med 181; 2010:A4461.
OPP D86—US Pharmacopeia, USP 31 vol. 1, pp. 605-607 as in force of May 1, 2008.
Experimental data on relative humidity (patentee's submission of 19.02.2018, cited in opposition of EP2611423).
FDA Guidance Metered Dose Inhaler (MDI) and Dry Powder Inhaler (DPI) Drug Products, Nov. 13, 1998; Chemistry, Manufacturing and Controls Documentations.
Ford, et al., "The therapeutic index of vilanterol trifenatate." Eur. Respir. J.; 2010; vol. 36, Suppl. 54: pp. 1184 (Abstract).

GlaxoSmithKline commences Relovair Phase III asthma programme; https://us/gsk.com/en-us/media/press-releases/2010/glaxosmithkline-commences-reloviar-phase-III-asthma-programme/; Dec. 17, 2015; pp.1-13.
Grounds for the Decision (Annex)—Opposition, EP2611423, May 17, 2018, pp. 1-17.
GSK Clinical Trial No. NCT01128569, Randomised Study Comparing the Effects on Inhaled Fluticasone Furoate (FF)/VIlanterol (VI; GW642444M) Combination and FF on an Allergen Induced Asthmatic Response, https://clinicaltrials.gov/ct2/show/study/NCT01128569?TERM=gw 642444m+fluticasone&rank=4; First received May 20, 2010; Last updated May 29, 2014; pp. 1-5.
Guchardi et al., "Influence of fine lactose and magnesium stearate on low dose dry powder inhaler formulations" International Journal of Pharmaceutics, vol. 348, Issues 1-2, Feb 4, 2008, pp. 10-17.
Guidance for Industry, "Metered dose inhaler (MDI) and dry powder inhaler (DPI) drug products, chemistry, manufacturing, and cold pulse documentation, graft guidance", US Department of Health and Human Services, Food and Drug Adminstration, Center for Drug Evaluation and Research (CDER), Oct. 1998.
Hajdu, D. et al., "Molecular Seives: Unique Moisture and Odor-Taste Control Material," Aug. 22-26, 1999; TAPPI Polymers, Lamination & Coatings Conference; Atlanta, vol. 2; pp. 655-662 (Abstract).
Hanania, et al., "Safety of vilanterol trifenatate (VI) in a COPD dose-ranging study," Eur Respir J; 2010; vol. 36, Suppl, 54; pp. 1185 (Abstract).
http://www.pharmpro.com/Archives/2006/10/Harnessing-The-Power-of-Desiccant-Technology-for-Inhalation-Therapies/.
HygroPalm HP23-A/HP23-AW-A-Hand-Held Indicator User Guide, Rotronic AG; 2009-2012; pp. 1-39.
ICH Topic E 4 Doses Response Information to Support Drug Registration; European Medicines Agency; Nov. 1994.
Jashnani et al., "Dry powder aersol generation in different environments: Performance comparisons of albuterol, albuterol sulfate, albuterol adipate and albuterol stearate", International Journal of Pharmaceutics; 1996; vol. 130; pp. 13-24.
Jashnani, et al., "Testing of dry powder aerosol formulations in different environment conditions" International Journal of Pharmaceuticals; 1995; vol. 133; pp. 123-130.
Lehto, et al., "Moisture Transfer into medicament chambers equipped with a double-barrier-desiccant system", International Journal of Pharmaceutics; 2004; vol. 275 (1/2); 155-164.
Multisorb Technologies, "Multisorb Introduces Desiccant Integration Approaches to Preserve the Function of Respiratory Drug Devices and their Drug Product Formulations—New Generation of Multiform Coated Solid Form Sorbents Provide Enhanced Protection for Reservoir Dry Powder"; Jan. 7, 2007: http://multisorb.com/news-andevents/news/multisorb-introduces-desiccant-integration-approaches-to-preserve-the-function-of-respiratory-drug-devices-and-their-drug-product-formulations-new-generation-of-multiform-coated-solid-form-sorbents-provide-en].
NIH guidelines on Asthma Treatment; Aug. 28, 2007.
OPP D87—Drugs for the treatment of respiratory diseases, edited by D. Spina et al.; Cambridge University Press 2003.
OPP D88—Definition of the term "respiratory disease" downloaded on Feb. 12, 2020 from the online NCI Dictionary of Cancer Terms https://www.cancer.gov/publications/dictionaries/cancerterms/def/respiratory-disease.
OPP D50—B. Mei Jin Tanm L. Wah Chan and P. Wan Sia Heng, „Chapter 11 Milling and Blending: Producing the Right Particles and Blend Characteristics for Dry Powder Inhalation Pharmaceuticals Inhalation Aerosol Technology Third Edition 2019, p. 273-284.
Decision T 0007/07; Jul. 7, 2011.
Opposition Submission to EP2400950 by HGF filed Feb. 21, 2020.
Opposition Submission to EP2400950 by Teva filed Feb. 22, 2020.
Opposition Submission to EP2400950 by NLO filed Feb. 21, 2020.
Opposition Submission to EP2400950 by Sandoz filed Feb. 24, 2020.
OPP 1—Arven/Wuesthoff Brief in oppostion to European patent No. 2400950 to Glaxo Group Limited dated Feb. 14, 2020.
OPP 2—Strawman/Dehns Brief in opposition to European patent No. 2400950 to Glaxo Group Limited dated Feb. 18, 2020.

(56) References Cited

OTHER PUBLICATIONS

OPP 1—D1—(Submission of GGL in examination of Eur. Pat. Appl. 09 779 096.8-1219 (which issued as opposed patent EP 2400950) dated Feb. 4, 2013).
OPP 2 D5—Biospace News Release dated Feb. 4, 2009.
OPP 2 D6—Fierce Biotech News Release dated Dec. 2, 2008.
OPP 2 D8—Clinical Trial Protocol NCT00766090, Oct. 2, 2008.
OPP 3 D1—Clinical Trial Protocol for Clinical Trial with Identifier NCT00606684.
OPP 3 D3—Declaration of Helsinki; Oct. 2008.
OPP 3 D4—Decision T 0007/07; Jul. 7, 2011.
OPP 3 D6—Decision T 0239/16; Sep. 13, 2017.
OPP 3 D7—NIH guidelines on Asthma Treatment; Aug. 28, 2007.
OPP 3 D9—Theravance Press Release dated Apr. 2, 2007.
OPP 3 D10—Donohue, "Minimal Clinically Important Differences in COPD Lung Function." COPD: Journal of Chronic Obstructive Pulmonary Disease; 2005; pp. 111-124; vol. 2.
OPP 3 D11—ICH Topic E 4 Dose Response Information to Support Drug Registration; European Medicines Agency; Nov. 1994.
OPP 3/4—GJE Notice of Opposition to European patent No. 2400950 to Glaxo Group Limited dated Feb. 20, 2020.
OPP 3/4—AERA Notice of Opposition to European patent No. 2400950 to Glaxo Group Limited dated Feb. 20, 2020.
RD541024, Mar. 4, 2020.
"PCT Application No. PCT/EP2009052306, Notification of Withdrawal of Priority Claim" dated Aug. 18, 2009.
"Rule 20.6 PCT Communication with Missing Pages and Drawingss" PCT/EP2011/06055, filed Jan. 29, 2013.
AERA Notice of Opposition to European patent No. 2400950 to Glaxo Group Limited dated Feb. 20, 2020.
Anderson, et al., "A Guide to the Measurement of Humidity", The Institute of Measurement and Control; 1996.
Angberg, M. et al., "Evaluation of heat-conduction microcalorimetry in pharmaceutical stability studies. IV. The influence of microcrystalline cellulose on the hydration rate of anhydrous lactose" 1991; International Journal Pharmaceutics; vol. 77(2-3); pp. 269-277.
Annex, Submission dated Apr. 24, 2015 in the European patent application No. 11 755 042.6 filed by the same Applicant, cited in opposition of EP2611423.
Anonymous, RD541024A, "Package for receiving medical device e.g. dry powder inhaler, has moisture absorbent unit absorbing gaseous and/or liquid substance in puch, where adsorbent unit includes chemically and biologically inert sachet comprising silica gel." May 10, 2009.
Aulton, "Pharmaceutics. The Science of Dosage Form Design" Second Edition; Churchill Livingstone; 2002.
Australian Patent Application No. 2011 298 409, Applicant's Response to Examination Report dated Aug. 12, 2013, the response filed Oct. 22, 2013.
Australian Patent Application No. 2011 298 409, Examination Report dated Aug. 12, 2013.
Bell, "A Beginner's Guide to Humidity Measurement", National Physical Laboratory; 2011.
Bleecker, et al., "Consistently favorable safety profile of Fluticasone (FF), a once-daily (od) inhaled corticosteroid (ICS), across a range of treatment steps in patients with uncontrolled asthma", American Thoracic Society International Conference Abstracts: C31 Optimizing therapeutic strategies in airways disease, thematic poster session, May 15, 2011.
Busse, et al., "Fluticasone Furoate (FF), A Once-Daily Inhaled Corticosteroid (ICS). In efficacious in patients with uncontrolled asthma across a range of treatment steps", American Thoracic Society International Conference Abstracts: C31 Optimizing therapeutic strategies in airways disease, thematic poster session, May 15, 2011.
Calverley et al., "Fluticasone furoate, vilanterol and lung function decline in patients with moderate COPD and heightened cardiovascular risk", AJRCCM, pp. 47-55, Jul. 24, 2017.

Cazzola, et al., "Beta2-adrenoceptor agonists: current and future direction" British Journal of Pharmacology; 2011, vol. 163; pp. 4-17.
ClinicalTrials Identifier: NCT01128569 "A Randomised, Double-blind, Placebo-controlled, Three-way Crossover, Repeat Dose Pilot Study Comparing the Effect of Inhaled Fluticasone Furoate/GW642444M Combination and Fluticasone Furoate on the Allergen-induced Early Asthmatic Response in Subjects With Mild Asthma",ClinicalTrials.gov archive: First received May 20, 2010; Last updated May 29, 2014.
ClinicalTrials Identifier: NCT01134042 "HZA106829: A Randomised, Double-blind, Parallel Group, Multicentre Study of Fluticasone Furoate/GW642444M Inhalation Powder Fluticasone Furoate Inhalation Powder Alone, and Fluticasone Propionate Alone in the Treatment of Persistent Asthma in Adults and Adolescents",ClinicalTrials.gov archive: First received May 27, 2010; Last updated Jun. 6, 2013.
Committee for medicinal products for human use: Guideline on the pharmaceutical quality of inhalation and nasal products, London, Jun. 21, 2006.
Communication of Notice of Opposition for EP Application No. 11755043.4 (Teva UK Ltd.) dated Apr. 1, 2016.
Communication of Notice of Opposition for EP Application No. 11755043.4 (Generics UK Ltd.) dated Mar. 31, 2016.
Communication of Notice of Opposition for EP Application No. 11755043.4 (Oser Andreas) dated Mar. 31, 2016.
El-Gendy et al., "Development of Budesonide NanoCluster Dry Powder Aerosols; Formulation and Stability." Journal of Pharmaceutical Sciences, vol. 101, No. 9 (Sep. 2012) pp. 3445-3455.
EP Patent No. 2611423, Patentee's Response to the Opposition dated Dec. 6, 2016.
EP1232745 Decision of the Emlarged Board of Appeal in review procedure dated Jul. 30, 2012.
EP1232745 Notice of Opposition dated Dec. 10, 2007, pp. 1-5.
EP1232745 Notice of Oppostion dated Dec. 6, 2007, pp. 1-4.
EP1232745 Reply of the Patent Proprieter to the Notice(s) of Oppositions dated Oct. 9, 2008.
EP1232745 Reply of the Patent Proprieter to the Notice(s) of Oppositions dated Sep. 25, 2008.
EP1232745 Statement of Grounds of Appeal dated Mar. 25, 2010.
EP1232745 Written Submission in Preparation to/during Oral Proceedings dated Aug. 27, 2009, pp. 1-34.
OPP D27—T950/13, Mar. 3, 2001.
OPP D28—www.clinicaltrial.gov; Identifier NCT00463697 dated Oct. 15, 2008 "A Randomized, Singledose, Dose-ascending, Double Blind, Placebo-controlled, 5-way Crossover Study to Investigate the Safety, Tolerability, Pharmacokinetics and Pharmacodynamics of Inhaled Doses of GW642444M With Magnesium Stearate in Asthmatic Patients" Available from: https://clin icaltrials.gov/ct2/history/NCT00463697?V_5=View#StudyPage Top.
OPP D28—www.clinicaltrial.gov; Identifier NCT00463697 dated Jul. 15, 2010 "A Randomized, Singledose, Dose-ascending, Double Blind, Placebo-controlled, 5-way Crossover Study to Investigate the Safety, Tolerability, Pharmacokinetics and Pharmacodynamics of Inhaled Doses of GW642444M With Magnesium Stearate in Asthmatic Patients" Available from: https://clin icaltrials.gov/ct2/history/NCT00463697?V_7=View#StudyPage Top.
OPP D31—T712/13 Mar. 3, 2001.
OPP D32—Ansel's Pharmaceutical Dosage Forms and Drug Delivery Systems, Eighth Edition, Eds. L.V. Allen, Jr et al., Lippincott Williams & Wilkins, 2005, chapters 2 and 6.
OPP D33—R. Schmidt "Dose-Finding Studies in Clinical Drug Development" Eur J Clin Pharmacol 1988, 34, 15-19.
OPP D34—Guideline for Industry Dose Response Information to Support Drug Registration ICH-E4 FDA, Nov. 1994. Available from: https://www.fda.gov/regulatory-information/search-fdaguidance- documents.
OPP D35—BNF (British National Formulatory), Sep. 2008, London, pp. 151-155.
OPP D36—Actavis & Orc v ICOS & Or [2017] EWCA Civ 1671.
OPP D37—Actavis Group PTC EHF and others v ICOS Corporation and another [2019] UKSC 15.
OPP D38—T1753/06 03.03.01.

(56) References Cited

OTHER PUBLICATIONS

OPP D39—Expert declaration provided by Mr Gary Muirhead; Feb. 18, 2020.
OPP D39A—Curriculum Vitae of Mr Gary Muirhead.
OPP D40—Zeng et al., Particle interactions in dry powder formulations for inhalation, Taylor & Francis, London and New York, 2001; Chapter 5, pp. 144-159.
OPP D41—www.clinicaltrial.gov; Identifier NCT00519376 dated Oct. 9, 2008 "A Randomised, Singledose, Dose Ascending, Double-blind, Placebo Controlled, Four-way, Incomplete Block Crossover Study to Investigate the Safety, Tolerability, Pharmcokinetics and Pharmcodynamics of Inhaled Doses of GW642444M With Magnesium Stearate in COPD Patients" Available from: https://clinicaltrials.gov/ct2/history/NCT00519376?V_3=View#Study Page Top.
OPP D42—www.clinicaltrial.gov; Identifier NCT00606684 dated Nov. 6, 2008 "Study B2C111045, A Dose-Finding Study of GW642444 Versus Placebo in Patients with COPD" Available from: https://clinicaltrials.gov/ct2/history/NCT00606684?V_11=View#StudyPage Top.
OPP D44—S Newham Evolution of dry powder inhaler design, formulation, and performance, Res Med., v96,2002,293-294.
OPP D45—H. Chrystyn, "The DiskusTM: a review of its position among dry powder inhaler devices", International Journal of Clinical Practice, 61, 6, 1022-1036, Jun. 2007.
OPP D46—S. Newman "How Well Do In Vitro Particle Size Measurements Predict Drug Delivery In Vitro?" Journal of Aerosol Medicine 1998, 11, S97-S104.
OPP D47—T. Peng, S. Lin, B. Niu, X. Wang, Y. Huang, X. Zhang, G. Li, X. Pan and C. Wu "Influence of physical properties of carrier on the performance of dry powder inhalers" Acta Pharmaceutica Sinica B 2016, 6, 308-318.
Lotvall, et al., "24-h duration of the novel LABA violanterol trifenatate in asthma patients treated with inhaled corticosteroids," *Eur. Respir. J.*, 40:570-579 (2012).
Sterling, et al., "Efficacy and optimal dosing interval of the long-acting beta$_2$ agonist, vilanterol, in persistent asthma: A randomised trial," *Respiratory Medicine*, 106:1110-1115 (2012).
Zeng, Particle interactions in dry powder formulations for inhalation: Department of Pharmacy: Kings College London, Chapter 5; ppp. 131-173 (2001).
P.J. Barnes "The Role of Anticholinergics in Chronic Obstructive Pulmonary Disease" Am J. Medicine, 117(12A): 24S-32S (2004).
British National Formulary 58, Sep. 2009, RPS Publishing, London, p. 168.
Cazzola et al., "Outcomes for COPD pharmacological trials: from lung function to biomarkers", European Respiratory Journal 31 (2008), pp. 41-468.
Clinical Study NCT00606684 as downloaded from clinicaltrials.gov.
Clinical Study NCT00732472 as downloaded from clinicaltrials.gov.
Consent from concerning clinical study NCT00606684.
Consent from concerning clinical study NCT00732472.
Consent from concerning clinical study NCT00976144.
Declaration of Helsinki 2008 version.
GSK Press release relating to Trelegy Ellipta.
Rule 116 EPC submission, Opposition of EP 2506844, Appl. No. 10781527.6 by Teva UK Limited (Oppo 01), Jul. 23, 2020.
Rule 116 EPC submission, Opposition of EP 2506844, Appl. No. 10781527.6 by Dr. Markus Breuer (Oppo 02), Jul. 22, 2020.
Rule 116 EPC submission, Opposition of EP 2506844, Appl. No. 10781527.6 by Sima Patent Lisanslama Hizetleri Ltd STI (Oppo 03), Jul. 13, 2020.
Study Report relating to clinical study NCT00976144 as downloaded from http://www.gsk-studyregiester.com/en/.
Tai-Singer et al., "Initial assessment of single and repeat doses of inhaled umeclidiniumin patients with chronic obstructive pulmonary disease: Two randomised studies", European Journal of Pharmacology 701 (2013), pp. 40-48.

COMBINATIONS OF A MUSCARINIC RECEPTOR ANTAGONIST AND A BETA-2 ADRENORECEPTOR AGONIST

This application is a Divisional Application of U.S. patent application Ser. No. 14/970,945, filed 16 Dec. 2015, now U.S. Pat. No. 9,750,726, which is a Continuation Application of U.S. patent application Ser. No. 13/510,962, filed Aug. 20, 2012, abandoned, which is a § 371 national stage entry of International Patent Application No. PCT/EP2010/068429, filed 29 Nov. 2010, which claims priority to GB 0921075.8, filed Dec. 1, 2009, each of which are incorporated by reference herein in their entireties.

FIELD OF THE INVENTION

This invention relates to pharmaceutical products an compositions for use in the treatment of chronic obstructive pulmonary disease (COPD), asthma and related diseases.

More particularly this invention relates to the combination of muscarinic receptor antagonist and a beta-2 adrenoreceptor agonist, and the use of said combination in treating diseases mediated via the $M_3$ muscarinic acetylcholine receptor and/or the beta-2 adrenoreceptor.

More particularly this invention is concerned with no pharmaceutical combination products comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate and 4-[hydroxy(diphenyl)methyl]-1-{2-[(phenylmethyl)oxy]ethyl}-1-azoniabicyclo[2.2.2]octane bromide and the use of said combination products in medicine, particularly in treating diseases mediated via the $M_3$ muscarinic acetylcholine receptor and/or the beta-2 adrenoreceptor, for example in the prophylaxis and treatment of inflammatory or respiratory tract diseases.

BACKGROUND OF THE INVENTION

Selective $\beta_2$-adrenoreceptor agonists have been used in the prophylaxis and treatment of clinical conditions for which a bronchodilating agent has been indicated. Such conditions include diseases associated with airflow obstruction such as chronic obstructive pulmonary diseases (COPD) (e.g. chronic and wheezy bronchitis, emphysema), asthma, respiratory tract infection and upper respiratory tract disease (e.g. rhinitis, including seasonal and allergic rhinitis).

In particular, asthma and other related disorders are typically treated with beta-2 adrenergic receptor agonists (beta-2 agonists) as they provide a bronchodilator effect to the patient, resulting in relief from the symptoms of breathlessness. Within the beta-2 agonist class there are presently available short acting compounds for immediate relief, such as salbutamol, biltolterol, pirbuterol and terbutaline. There are also longer acting compounds commercially available, such as salmeterol and formoterol. Salmeterol is available by prescription for use twice daily in the treatment of asthma.

Over the last two decades, inhaled anticholinergic agents have become well established as well-tolerated and effective bronchodilators for the treatment of COPD. Treatment with anticholinergics significantly improves $FEV_1$, (forced expiratory volume in 1 second) resting and dynamic lung hyperinflation, symptoms and exercise capacity, and reduces COPD exacerbations. Currently, only a few inhaled anticholinergic bronchodilators are available: the short-acting ipratropium bromide (ipratropium; dosed four-times-a-day) and oxitropium bromide, and the long-acting tiotropium bromide (tiotropium; dosed once-daily).

WO 03/024439 describes compounds of the general formula:

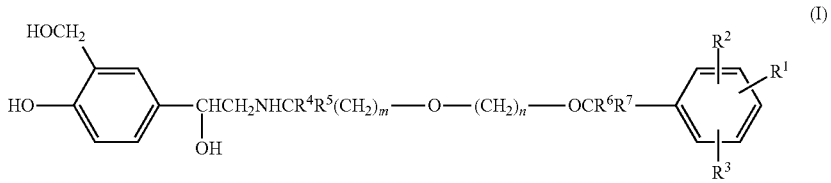

(I)

and salts, solvates, and physiologically functional derivatives thereof.

The compound 4-{(1R)-2-[(6-{2-[(2,6-dichlorobenzyl)oxy]ethoxy}hexyl)amino]-1-hydroxyethyl}-2-(hydroxymethyl)phenol is specifically described in WO03/02443, as are pharmaceutically acceptable salts thereof, in particular the acetate, triphenylacetate, α-phenylcinnamate, 1-naphthoate and (R)-mandelate salts.

WO2005/104745 describes compounds of the formulae:

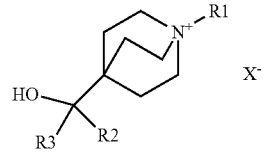

WO2005/104745 specifically describes the compound 4-[hydroxy(diphenyl)methyl]-1-{2-[(phenylmethyl)oxy]ethyl}-1-azoniabicyclo[2.2.2]octane bromide.

SUMMARY OF THE INVENTION

In a first aspect the present invention provides a novel pharmaceutical combination product comprising the therapeutic agents:
a) a compound of the formula:

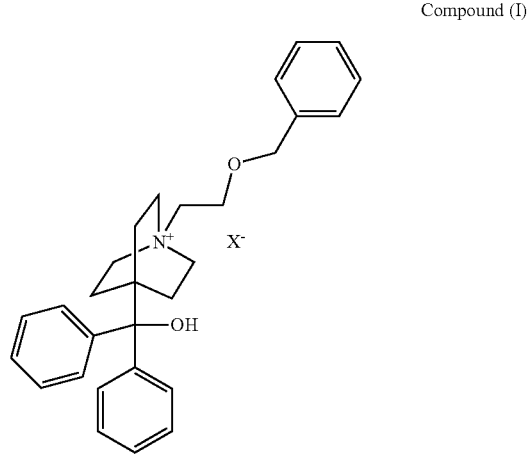

Compound (I)

wherein
X⁻ is a pharmaceutically acceptable anion;
and
b) a compound of the formula:

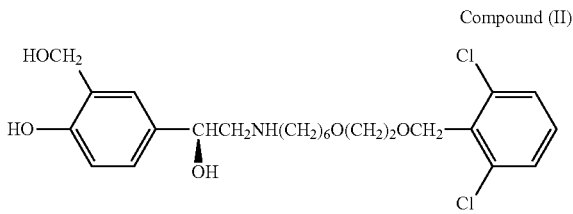
Compound (II)

or a pharmaceutically acceptable salt thereof.

Hereinafter, Compound (II) may refer to the free base depicted above, and/or one or more salts thereof, as dictated by the context.

In one embodiment the pharmaceutical combination product comprises 4-{(1R)-2-[(6-{2-[(2,6-dichlorobenzyl)oxy]ethoxy}hexyl)amino]-1-hydroxyethyl}-2-(hydroxymethyl)phenol triphenylecetate and 4-[hydroxy(diphenyl)methyl]-1-{2-[(phenylmethyl)oxy]ethyl}-1-azoniabicyclo[2.2.2]octane bromide.

In one embodiment 4-{(1R)-2-[(6-{2-[(2,6-dichlorobenzyl)oxy]ethoxy}hexyl)amino]-1-hydroxyethyl}-2-(hydroxymethyl)phenol triphenylacetate and 4-[hydroxy(diphenyl)methyl]-1-{2-[(phenylmethyl)oxy]ethyl}-1-azoniabicyclo[2.2.2]octane bromide are the sole active ingredients in said pharmaceutical combination product.

In another embodiment the pharmaceutical combination product of Compound (I) and Compound (II) additionally comprises an inhaled corticosteroid.

This invention also provides for use of the pharmaceutical combination product in the manufacture of a medicament for the treatment of conditions for which administration of one or more of the therapeutic compounds is indicated.

In one embodiment the use is for the manufacture of a medicament for the treatment of inflammatory or respiratory tract diseases, by simultaneous or sequential administration of Compound (I) and Compound (II).

In another embodiment the use is for the manufacture of a medicament for the treatment of chronic obstructive pulmonary disease (COPD) and/or asthma, by simultaneous or sequential administration of Compound (I) and Compound (II).

The invention also provides said pharmaceutical combination product for use in the treatment of inflammatory or respiratory tract diseases, such as chronic obstructive pulmonary disease (COPD) and/or asthma.

Another embodiment of the invention is a method for the treatment of inflammatory or respiratory tract diseases, comprising administering ether sequentially or simultaneously, to a patient in need thereof, a pharmaceutical combination product comprising Compound (I) and Compound (II).

In one embodiment of the invention the inflammatory or respiratory tract disease is selected from the group consisting of chronic obstructive pulmonary disease, chronic bronchitis, asthma, chronic respiratory obstruction, pulmonary fibrosis, pulmonary emphysema, allergic rhinitis, small airways disease, bronchiectasis and cystic fibrosis.

In another embodiment of the invention the pharmaceutical combination product may be used for the treatment of inflammatory or respiratory tract diseases, and more specifically the treatment of chronic obstructive pulmonary disease (COPD) and/or asthma by simultaneous or sequential administration of Compound (I) and Compound (II).

DETAILED DESCRIPTION OF THE INVENTION

The present invention is directed to a pharmaceutical combination product comprising
a) compound of formula:

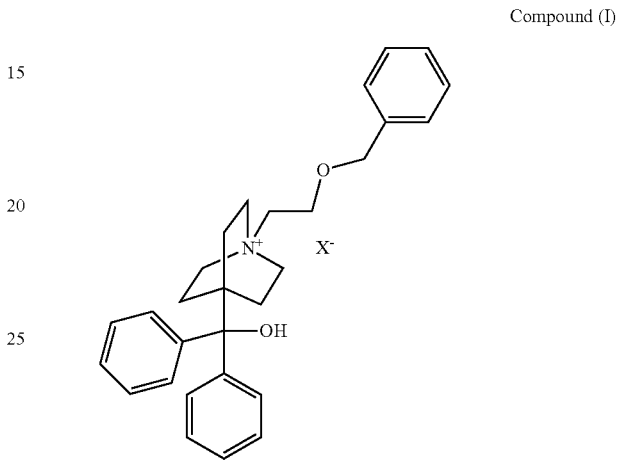
Compound (I)

wherein
X⁻ is a pharmaceutically acceptable anion;
and
b) a compound of formula:

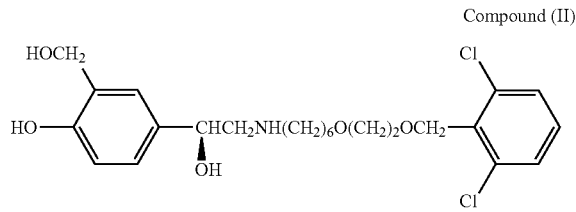
Compound (II)

or a pharmaceutically acceptable thereof.

The pharmaceutically acceptable anion depicted by X⁻ may be selected from chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate. In one embodiment the pharmaceutically acceptable anion X⁻ is bromide.

For purposes herein, the structural formula for the quaternary moiety (cation) of Compound (I) is also referred to as 4-[hydroxy(diphenyl)methyl]-1-{2-[(phenylmethyl)oxy]methyl}-1-azoniabicyclo[2.2.2]octane.

In one embodiment of the invention Compound (I) is 4-[hydroxy(diphenyl)methyl]-1-{2-[(phenylmethyl)oxy]ethyl}-1-azoniabicyclo[2.2.2]octane bromide (also referred to herein as Compound (I) bromide).

Pharmaceutically acceptable acid addition salts of Compound (II) include those formed from hydrochloric, hydrobromic, sulphuric, citric, tartaric, phosphoric, lactic, pyruvic, acetic, trifluoroacetic, triphenylacetic, phenylacetic, substituted phenyl acetic e.g. methoxyphenyl acetic, sulphamic, sulphanilic, succinic, oxalic, fumaric, maleic, malic, glutamic, aspartic, oxaloacetic, methanesulphonic, ethanesulphonic, arylsulponic (for example p-toluenesulphonic, benzenesulphonic, naphthalenesulphonic or naphthalenedisulphonic), salicylic, gultaric, gluconic, tricarballylic, mandelic, cinnamic, substituted cinnamic (for example, methyl, methoxy, halo or phenyl substituted cinnamic, including 4-methyl and 4-methoxycinnamic acid and α-phenyl cinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, bezeneacrylic (for example 1,4-benzenediacrylic) and isethionic acids.

In one embodiment the pharmaceutically acceptable salt of Compound (II) is selected from the acetate, 1-naphthoate and (R)-mandelate salts;

In another embodiment the pharmaceutically acceptable salt of Compound (II) is the α-phenylcinnamate salt.

In another embodiment the pharmaceutically acceptable salt of Compound (II) is the triphenylacetate salt.

The structural formula shown above for Compound (II) may be named as 4-{(1R)-2-[(6-{2-[(2,6-dichlorobenzyl)oxy]ethoxy}hexyl)amino]-1-hydroxyethyl}-2-(hydroxymethyl)phenol.

In one embodiment of the invention Compound (II) is 4-{(1R)-2-[(6-{2-[2,6-dichlorobenzyl)oxy]ethoxy}hexyl)amino]-1-hydroxyethyl}-2-(hydroxymethyl)phenol triphenylacetate (also referred to as Compound (II) triphenylacetate).

In one embodiment the pharmaceutical combination product the invention comprises 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In another embodiment the pharmaceutical combination product of Compound (I) and Compound (II) additionally comprises an inhaled corticosteroid, e.g. fluticasone propionate, mometasone furoate, budesonide or 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

In one embodiment said pharmaceutical combination product comprises 4-[hydroxy(diphenyl)methyl]-1-{2-[(phenylmethyl)oxy]ethyl}-1-azoniabicyclo[2.2.2]octane bromide, 4-{(1R)-2-[(6-{2-[(2,6-dichlorobenzyl)oxy]ethoxy}hexyl)amino]-1-hydroxyethyl}-2-(hydroxymethyl)phenol triphenylacetate and 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

In one embodiment, the pharmaceutical combination product of the invention comprises 4-[hydroxy(diphenyl)methyl]-1-{2-[(phenylmethyl)oxy]ethyl}-1-azoniabicylo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate as the sole active ingredients.

Compound (I), specifically 4-[hydroxy(diphenyl)methyl]-1-{2-[(phenylmethyl)oxy]ethyl}-1-azoniabicyclo[2.2.2]octane bromide has been the subject of studies in animal models, and in humans, and has been found to be a long acting high-affinity pan-active muscarinic receptor antagonist which has potential for once-daily administration.

Compound (II), 4-{(1R)-2-[(6-{2-[(2,6-dichlorobenzyl)oxy]ethoxy}hexyl)amino]-1-hydroxyethyl}-2-(hydroxymethyl)phenol and its salts has been extensively tested in animal and human studies and has been found to demonstrate sustained bronchodilation over a 24 hour period in conjunction with a favourable safety profile and thus has the potential for once-daily administration.

Compound (I) and Compound (II), and the combination thereof, are considered to have potential in the treatment of inflammatory or respiratory tract diseases such as chronic obstructive pulmonary disease, chronic bronchitis, asthma, chronic respiratory obstruction, pulmonary fibrosis, pulmonary emphysema, allergic rhinitis, small airways disease, bronchiectasis and cystic fibrosis.

COPD is a chronic disease characterised by airways obstruction and reduced maximum expiratory flow from the lungs that manifests as persistent daily symptoms, such as shortness of breath (dyspnoea), and limitation of the ability to perform daily activities or exertion. Furthermore, there are periodic exacerbations of the condition that result in worsening of the day-to-day symptoms and activity limitation, and can also lead to hospitalisation of the patient because of the severity of the worsening symptoms/limitation. In addition, there is a progressive decline in lung function (disease progression) over several years.

Bronchodilator treatment in COPD includes but is not necessarily limited to reducing symptoms, particularly dyspnoea, to allow a patient to undertake more daily activities and other activities that require exertion, and preventing exacerbations.

Asthma is a chronic condition, which is characterised by widespread, variable and reversible airflow obstruction. Symptoms include coughing, wheezing, breathlessness and/or a tight feeling in the chest. Asthma attacks are generally caused by exposure to a trigger, such as pollen, dust or other allergens, which causes constriction of the airways (bronchoconstriction). It will be appreciated that a subject suffering from a condition such as asthma, may variously from time to time display no overt symptoms or the condition, or may suffer from pericydic attacks during which symptoms are displayed or may experience exacerbations or worsening of the condition. In this context the term 'treatment' is intended to encompass prevention of such periodic attacks or exacerbations of the existing condition. Such treatment may be referred to as 'maintenance treatment' or 'maintenance therapy'.

The amounts of Compound (I) and Compound (II), and in one embodiment of the invention, 4-[hydroxy(diphenyl)methyl]-1-{2-[(phenylmethyl)oxy]ethyl}-1-azoniabicyclo[2.2.2]octane bromide and 4-{(1R)-2-[(6-{2-[(2,6-dichlorobenzyl)oxy]ethoxy}hexyl)amino]-1-hydroxyethyl}-2-(hydroxymethyl)phenol triphenylacetate, required to achieve a therapeutic effect will, of course, vary with the route of administration, the subject under treatment, the particular disorder or disease being treated, and the severity of the disease. In one embodiment, the route of administration is by inhalation via the mouth or nose. In a further embodiment, the route of administration is by inhalation via the mouth.

In one embodiment Compound (I), and specifically (4-[hydroxy(diphenyl)methyl]-1-{2-[(phenylmethyl)oxy]ethyl}-1-azoniabicyclo[2.2.2]octane bromide, may be administered by inhalation at a dose of from about 1 mcg to about 1000 mcg/daily, e.g. 100, 250 or 500 mcg per day. In a further embodiment, Compound (I) and specifically (4-[hydroxy(diphenyl)methyl]-1-{2-[(phenylmethyl)oxy]ethyl}-1-azoniabicyclo[2.2.2]octane bromide may be administered by inhalation at a dose of 62.5 mcg or 125 mcg per day. In general Compound (I) will be administered as a once-daily dose.

In a further embodiment, Compound (I), and specifically (4-[hydroxy(diphenyl)methyl]-1-{2-[(phenylmethyl)oxy]ethyl}-1-azoniabicyclo[2.2.2]octane bromide, may be administered by inhalation, once-daily, at a dose of 62.5 mcg per day.

In a further embodiment, Compound (I), and specifically (4-[hydroxy(diphenyl)methyl]-1-{2-[phenylmethyl)oxy]ethyl}-1-azoniabicyclo[2.2.2]octane bromide, may be administered by inhalation, once-daily, at a dose of 125 mcg per day.

Compound (II) may for example be administered by inhalation at a dose of from 1 mcg to about 400 mcg/day (calculated as the free base). In one embodiment Compound (II) and specifically 4-{(1R)-2-[(6-{2-[(2,6-dichlorobenzyl)oxy]ethoxy}hexyl)amino]-1-hydroxyethyl}-2-(hydroxymethyl)phenol triphenylacetate, may be administered by inhalation at a dose of from about 1 mcg to 100 mcg/day, for example 3, 6.25, 12.5, 25, 50 or 100 mcg/day (calculated as the free base). In general Compound (II) will be administered as a once-daily dose. In one embodiment Compound (II) may be administered by inhalation at a dose of 12.5 mcg/day. In another embodiment Compound (II) may be administered by inhalation at a dose of 25 mcg/day. In another embodiment Compound (II) may be administered by inhalation at a dose of 50 mcg/day.

In a further embodiment, 4-{(1R)-2-[(6-{2-[(2,6-dichlorobenzyl)oxy]ethoxy}hexyl)amino]-1-hydroxyethyl}-2-(hydroxymethyl)phenol triphenylacetate, may be administered by inhalation, once-daily, at a dose of 25 mcg per day.

In a further embodiment, the present invention provides pharmaceutical combination product for once-daily administration by inhalation, comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate at a dose of 25 mcg per day, and (4-[hydroxy(diphenyl)methyl]-1-{2-[(phenylmethyl)oxy]ethyl}-1-azoniabicyclo[2.2.2]octane bromide at a dose of 125 mcg per day.

In a further embodiment, the present invention provides a pharmaceutical combination product for once-daily administration by inhalation, comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate at a dose of 25 mcg per day, and (4-[hydroxy(diphenyl)methyl]-1-{2-[(phenylmethyl)oxy]ethyl}-1-azoniabicyclo[2.2.2]octane bromide at a dose of 62.5 mcg per day.

When the combination additionally includes an inhaled corticosteroid, this may be used at doses compatible with those known for monotherapy. When the inhaled corticosteroid is fluticasone furoate this may be administered by inhalation at a dose of from about 25 mcg to about 800 mcg daily, and if necessary in divided doses. Thus, the daily dose of fluticasone furoate may be for example 25, 50, 100, 200, 300, 400, 600 or 800 mcg, in general as a once-daily dose. In one embodiment, the daily dose of fluticasone furoate is 100 mcg. In a further embodiment, the daily dose of fluticasone furoate is 50 mcg.

The individual compounds of the pharmaceutical combination product as described herein may be administered either sequentially or simultaneously in separate or combined pharmaceutical formulations/compositions. Thus Compound (I) and Compound (II) may for example, be formulated separately and presented in separate packs or devices, or said individually formulated components may be presented in a single pack or device. Where appropriate, the individual compounds may be admixed within the same formulation, and presented as a fixed pharmaceutical combination. In general such formulations will include pharmaceutical carriers or excipients as described hereinafter, but combinations of the compounds without any excipients are also within the ambit of this invention. In one embodiment, the individual compounds of the pharmaceutical combination product may be administered simultaneously in a combined pharmaceutical formulation or composition.

When the pharmaceutical combination product additionally an inhaled corticosteroid, eg 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) this may likewise be formulated separately, either with or without one or more pharmaceutical carriers or excipients, and presented for either sequential or simultaneous administration, or the inhaled corticosteroid may be admixed with either Compound (I) and/or Compound (II), 6α,9α-Difluoro-17α-[(2-furanylcarbonyl)oxy]-11β-hydroxy-16α-methyl-3-oxo-androsta-1,4-diene-17β-carbothioic acid S-fluoromethyl ester may be formulated for example as described in WO02/12265, or as described hereinafter.

In further aspects the invention therefore provides:

A pharmaceutical combination product comprising Compound (I) and Compound (II) presented separately for sequential or simultaneous administration;

A pharmaceutical combination product comprising Compound (I) and Compound (II) presented separately but held in the same pack or device, for sequential or simultaneous administration; and A pharmaceutical combination product comprising Compound (I) and Compound (II) in admixture with each other for simultaneous administration.

In each case, each of Compound (I) and/or Compound (II) may be formulated with or without pharmaceutical carriers or excipients.

The present invention further provides a pharmaceutical combination product comprising Compound (I) and Compound (II) wherein at least one of Compound (I) and Compound (II) is formulated with a pharmaceutically acceptable carrier or excipient.

The present invention further provides a pharmaceutical combination product comprising Compound (I) and Compound (II) wherein each of Compound (I) and Compound (II) is formulated with a pharmaceutically acceptable carrier or excipient.

In one embodiment of this invention compositions of Compounds (I) and (II) include those suitable for inhalation, including fine particle powders, or mists which may be generated and administered by means of various types of inhalers for example, reservoir dry powder inhalers, unit-dose dry powder inhalers, pre-metered multi-dose dry powder inhalers, nasal inhalers or pressurized metered dose inhalers, nebulisers or insufflators.

The compositions may be prepared by any of the methods well known in the art of pharmacy. In general, said methods include the step of bringing the active ingredient(s) into association with the carrier which constitutes one or more accessory ingredients. In general the compositions are prepared by uniformly and intimately bringing into association the active ingredient with liquid carriers or finely divided solid carriers or both and then, if necessary, shaping the product into the desired composition.

Powder compositions generally contain a powder mix for inhalation of the active ingredient and a suitable powder base (carrier/diluent/excipient substance) such as mono-, di or poly-saccharides (e.g. lactose or starch). Use of lactose is preferred. The lactose may be for example anhydrous lactose or α-lactose monohydrate. In one embodiment, the carrier is α-lactose monohydrate. Dry powder compositions may also include, in addition to the active ingredient and carrier, a further excipient (eg a ternary agent) such as a sugar ester, calcium stearate or magnesium stearate.

Alternatively, the active ingredient may be presented without excipients. For the avoidance of doubt use of the term 'composition' or 'formulation' herein refers to the active ingredients either with or without excipients or carriers.

The present invention further provides a pharmaceutical combination product comprising Compound (I) and Compound (II) wherein at least one of Compound (I) and Compound (II) is formulated with a pharmaceutically acceptable carrier and a ternary agent.

The present invention further provides a pharmaceutical combination product comprising Compound (I) and Compound (II) wherein Compound (II) is formulated with a pharmaceutically acceptable carrier and a ternary agent.

In another embodiment the present invention further provides a pharmaceutical formulation comprising a combination of Compound (I) and Compound (II) wherein both Compounds are formulated with a pharmaceutically acceptable carrier and a ternary agent.

The present invention further provides a pharmaceutical combination product for inhaled administration comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate and (4-[hydroxy(diphenyl)methyl]-1-{2-[(phenylmethyl)oxy]ethyl}-1-azoniabicyclo[2.2.2]octane bromide each formulated separately with a pharmaceutically acceptable carrier and a ternary agent, but held in the same pack or device, for sequential or simultaneous administration.

In one embodiment said ternary agent is magnesium stearate.

The present invention further provides a pharmaceutical combination product for inhaled administration comprising 4-{(1R)-2-[(6-{2-[(2,6-dichlorobenzyl)oxy]ethoxy}hexyl)amino]-1-hydroxyethyl}-2-(hydroxymethyl)phenol triphenylacetate and (4-[hydroxy(diphenyl)methyl]-1-{2-[(phenylmethyl)oxy]ethyl}-1-azoniabicyclo[2.2.2]octane bromide each formulated separately with lactose as a pharmaceutically acceptable carrier, and magnesium stearate, as a ternary agent, but held in the same pack or device, for sequential or simultaneous administration.

The compositions may be presented in unit dosage form. Dry powder compositions for topical delivery to the lung by inhalation may, for example, be presented in capsules and cartridges of for example gelatine, or blisters of for example laminated aluminium foil, for use in an inhaler or insufflator.

Each capsule, cartridge or blister may generally contain between 1 mcg-1000 mcg, e.g. 100 to 500 mcg of Compound (I) and/or between 1 mcg-400 mcg, e.g. 1 to 100 mcg of Compound (II). Packaging of the formulation may be suitable for unit dose or multi-dose delivery. As indicated above Compound (I) and Compound (II) may be formulated independently or in admixture. Said compounds may thus be incorporated in separate unit doses or may be combined in a single unit dose with or without additional excipients as deemed necessary.

In a further embodiment, each capsule, cartridge or blister may contain 125 mcg or 62.5 mcg of Compound (I) and/or 25 mcg of Compound (II).

In yet a further embodiment, each capsule, cartridge or blister may contain 125 mcg or 62.5 mcg of (4-[hydroxy (diphenyl)methyl]-1-{2-[(phenylmethyl)oxy]ethyl}-1-azoniabicyclo[2.2.2]octane bromide and/or 25 mcg of 4-{(1R)-2-[(6-{2-[(2,6-dichlorobenzyl)oxy]ethoxy}hexyl)amino]-1-hydroxyethyl}-2-(hydroxymethyl)phenol triphenylacetate.

In one embodiment, a composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline. The DISKUS™ inhalation device is, for example, described in GB 2242134A.

A dry powder inhalable composition, may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ of AstraZeneca, TWISTHALER™ of Schering and CLICKHALER™ of Innovata.

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ of GlaxoSmithKline and HANDIHALER™ of Boehringer Ingelheim.

A dry powder composition may also be presented in a delivery device which permits separate containment of Compound (I) and Compound (II) optionally in admixture with one or more excipients. Thus, for example, the individual compounds of the combination are administrable simultaneously but are stored separately, e.g. in separate pharmaceutical compositions, for example as described in WO 2003/061743 A1, WO 2007/012871 A1 and/or WO2007/068896. In one embodiment a delivery device permitting separate containment of actives is an inhaler device having two medicament packs in peelable blister strip form, each pack containing pre-metered doses in blister pockets arranged along its length. Said device has an internal indexing mechanism which, each time the device is actuated, peels opens a pocket of each strip and positions the packs so that each newly exposed dose of each pack is adjacent a manifold which communicates with a mouthpiece of the device. When the patient inhales at the mouthpiece, each dose is simultaneously drawn out of its associated pocket into the manifold and entrained via the mouthpiece into the patient's respiratory tract. Thus, each time the device is used, the patient is administered a combination therapy consisting of a dose from each medicament pack. A further device that permits separate containment of different compounds is DUOHALER™ of Innovata.

In a further embodiment, the present invention provides a dry powder inhaler (Inhaler 1) comprising two compositions presented separately, wherein a first composition comprises
  i. 4-[hydroxy(diphenyl)methyl]-1-{2-[(phenylmethyl) oxy]ethyl}-1-azoniabicyclo[2.2.2]octane bromide, and
  ii. lactose, and
  iii. magnesium stearate at an amount of about 0.6% w/w based on the total weight of the first composition;
and a second composition comprises
  i. 4-{(1R)-2-[6-{2-[(2,6-dichlorobenzyl)oxy] ethoxy}hexyl)amino]-1-hydroxyethyl}-2-(hydroxymethyl)phenol triphenylacetate, and
  ii. lactose, and
  iii. magnesium stearate at an amount of about 1.0% w/w based on the total eight of the second composition.

In a further embodiment, the present invention provides Inhaler 1 wherein each composition is in unit dose form.

In a further embodiment, the present invention provides Inhaler 1 wherein the unit dose form is a capsule, cartridge or blister.

In a further embodiment, the present invention provides Inhaler 1 wherein 4-[hydroxy(diphenyl)methyl]-1-{2-[(phenylmethyl)oxy]ethyl}-1-azoniabicyclo[2.2.2]octane bromide is present in an amount of about 125 mcg/dose.

In a further embodiment, the present invention provides Inhaler 1 wherein 4-{(1R)-2-[(6-{2-[(2,6-dichlorobenzyl)oxy]ethoxy}hexyl)amino]-1-hydroxyethyl}-2-(hydroxymethyl)phenol triphenylacetate is present in an amount of about 25 mcg/dose.

In a further embodiment, the present invention provides Inhaler 1 wherein the second composition further comprises 6α,9α-(difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

In a further embodiment, the present invention provides Inhaler 1 wherein 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

Spray compositions for inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the pharmaceutical product and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid derivative e.g. as described in WO94/21229 and WO98/34598 and/or cosolvents e.g. ethanol. Pressurised formulations will generally be retained in a canister (e.g. an aluminium canister) closed with a valve (e.g. a metering valve) and fitted into an actuator provided with a mouthpiece.

There is thus provided as a further aspect of the invention a pharmaceutical combination product comprising Compound (I) and Compound (II) formulated individually or in admixture, with a fluorocarbon or hydrogen-containing chlorofluorocarbon as propellant, optionally in combination with a surface-active agent and/or a co-solvent. According to another aspect of the invention, the propellant is selected from 1,1,1,2-tetrafluoroethane, 1,1,1,2,3,3,3-heptafluoro-n-propane and mixtures thereof.

Another aspect of the invention is a pharmaceutical combination product consisting of Compound (I) and Compound (II) formulated individually or in admixture, with a fluorocarbon or hydrogen-containing chlorofluorocarbon as propellant, optionally in combination with a surface-active agent and/or a cosolvent. In another embodiment of the invention the propellant is selected from 1,1,1,2-tetrafluoroethane, or 1,1,1,2,3,3,3-heptafluoro-n-propane and mixtures thereof.

Where appropriate compositions according to the invention may be buffered by the addition of suitable buffering agents.

Active ingredients for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means e.g. by micronization. The desired fraction may be separated out by air classification or sieving. Preferably, the particles will be crystalline.

Dry powder compositions according to the invention may comprise a carrier. The carrier when it is lactose e.g. α-lactose monohydrate, may form from about 91 to about 99%, e.g. 97.7-99.0% or 91.0-99.2% by weight of the formulation. In general, the particle size of the carrier, for example lactose, will be much greater than the inhaled medicament within the present invention. When the carrier is lactose it will typically be present as milled lactose, having a MMD (mass median diameter) of 60-90 μm.

The lactose component may comprise a fine lactose fraction. The 'fine' lactose fraction is defined as the fraction of lactose having a particle size of less than 7 μm, such as less than 6 μm, for example less than 5 μm. The particle size of the 'fine' lactose fraction may be less than 4.5 μm. The fine lactose fraction, if present, may comprise 2 to 10% by weight of the total lactose component, such as 3 to 6% by weight fine lactose, for example 4.5% by weight fine lactose.

Magnesium stearate, if present in the composition, is generally used in an amount of about 0.2 to 2%, e.g. 0.6 to 2% or 0.5 to 1.75%, e.g. 0.6% to 0.75%, 1%, 1.25% or 1.5% w/w, based on the total weight of the composition. The magnesium stearate will typically have a particle size in the range 1 to 50 μm, and more particularly 1-20 μm, e.g. 1-10 μm. Commercial sources of magnesium stearate include Peter Greven, Covidien/Mallinckodt and FACI.

In a further embodiment there is provided a pharmaceutical combination product comprising Compound (I) and Compound (II) wherein Compound (I) is (4-[hydroxy(diphenyl)methyl]-1-{2-[(phenylmethyl)oxy]ethyl}-1-azoniabicyclo[2,2,2]octane bromide and is presented as a dry powder composition containing magnesium stearate at an amount of 0.6% w/w based on the total weight of the composition.

In yet a further embodiment, there is provided a pharmaceutical combination product comprising Compound (I) and Compound (II) wherein Compound (II) is 4-{(1R)-2-[(6-{2-[(2,6-dichlorobenzyl)oxy]ethoxy}hexyl)amino]-1-hydroxyethy}-2-(hydroxymethyl)phenol triphenylacetate and is presented as a dry powder composition containing magnesium stearate at an amount of 1.0% w/w based on the total weight of the composition.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulization may be formulated with an aqueous vehicle with the addition of agents such as acid or alkali, buffer salts, isotonicity adjusting agents or antimicrobials. They may be sterilized by filtration or heating in an autoclave, or presented as a non-sterile product.

The invention also provides a method of preparing a pharmaceutical combination product as defined herein, the method comprising either:

(a) preparing a separate pharmaceutical composition for administration of the individual compounds of the combination either sequentially or simultaneously, or (b) preparing a combined pharmaceutical composition for administration of the individual compounds together in the combination for simultaneous use, wherein the pharmaceutical composition comprises the combination together with one or more pharmaceutically acceptable carriers and/or excipients.

4-{(1R)-2-[(6-{2-[(2,6-dichlorobenzyl)oxy]ethoxy}hexyl)amino]-1-hydroxyethyl}-2-(hydroxymethyl)phenol, and its salts, including 4-{(1R)-2-[(6-{2-[(2,6-dichlorobenzyl)oxy]ethoxy}hexyl)amino]-1-hydroxyethyl}-2-(hydroxymethyl)phenol triphenylacetate may be prepared as described in WO03/024439 (Example 78(i)), which is incorporated by reference herein.

4-[hydroxy(diphenyl)methyl]-1-{2-[(phenylmethyl)oxy]ethyl}-1-azoniabicyclo[2.2.2]octane bromide is described as Example 84, in WO2005/104745 which is incorporated by reference herein.

Clinical Studies

4-[hydroxy(diphenyl)methyl]-1-{2-[(phenylmethyl)oxy]methyl}-1-azoniabicyclo[2.2.2]octane bromide 4-[hydroxy(diphenyl)methyl]-1-{2-[(phenylmethyl)oxy]ethyl}-1-azoniabicyclo[2.2.2]octane bromide has been found to be an effective long-acting potent, pan-active anti-muscarinic bronchodilator which demonstrates slow reversibility at the human M3 receptor in vitro and long duration of action in vivo when administered directly to the lungs in pre-clinical models. The long duration of action of this compound identified using in vitro models, when administered via inhalation in animals, and subsequently in early phase studies in healthy volunteers and COPD subjects supports the potential for use of this compound as a once daily bronchodilator for COPD.

Several clinical pharmacology studies have been conducted using 4-[hydroxy(diphenyl)methyl]-1-{2-[(phenylmethyl)oxy]ethyl}-1-azoniabicyclo[2.2.2]octane bromide in both healthy volunteers and COPD patients to investigate the safety, tolerability, pharmacokinetics and pharmacodynamics of this compound. The bronchodilatory effects and duration of action of single inhaled doses of this compound as measured by plethysmography ($sG_{aw}$, $R_{aw}$) and spirometry ($FEV_1$) were assessed in some of the above noted studies. These studies showed clinically relevant bronchodilation and 24 h duration of action for the compound.

In one such study, designed to evaluate the safety, efficacy and pharmacokinetics of 4-[hydroxy(diphenyl)methyl]-1-{2-[(phenylmethyl)oxy]ethyl}-1-azoniabicyclo[2.2.2]octane bromide in subjects with COPD, five once-daily doses (62.5 mcg, 125 mcg, 250 mcg, 500 mcg and 1000 mcg), taken over a 14-day treatment period, produced statistically significant improvements in pulmonary function compared to placebo. All once-daily doses showed numerically greater improvement in trough $FEV_1$ than the open label tiotropium active control (18 mcg once-daily). In addition, this study confirmed that 4-[hydroxy(diphenyl)methyl]-1-{2-[(phenylmethyl)oxy]ethyl}-1-azoniabicyclo[2.2.2]octane bromide has a once-daily profile.

A further study evaluated the efficacy and safety of three doses (125 mcg, 250 mcg and 500 mcg) of 4-[(hydroxy(diphenyl)methyl]-1-{2-[(phenylmethyl)oxy]ethyl}-1-azoniabicyclo[2.2.2]octane bromide administered once-daily via a dry powder inhaler over a 28 day period in subjects with COPD. This study confirmed that 4-[hydroxy(diphenyl)methyl]-1-{2-[(phenylmethyl)oxy]ethyl}-1-azoniabicyclo[2.2.2]octane bromide appears to be safe and efficacious, maintaining significant bronchodilation over twenty four hours.

Compound (II) (as the α-Phenylcinnamate Salt or the Triphenylacetate Salt)

Compound (II) as the α-phenylcinnamate salt and the triphenylacetate salt has been studied in a number of clinical pharmacology studies, including single- and repeat-dose studies. In addition, these studies have evaluated Compound (II) formulated with lactose and either cellobiose octaacetate or magnesium stearate. In asthmatic patients, a statistically and clinically significant improvement in trough (24-hour) FEV1 was observed for all doses of Compound (II) tested, compared to placebo. Single doses of 25 μg to 100 μg of Compound (II) triphenylacetate (containing lactose and magnesium stearate) demonstrated 24 hour duration of action as assessed by a 200 mL or greater increase in mean 23 to 24 hour post-dose FEV1 versus placebo.

In COPD patients, treatment with 100 mcg and 400 mcg Compound (II) alpha-phenylcinnamate (with lactose alone) achieved a clinically relevant adjusted mean difference from placebo in weighted mean through $FEV_1$ (22 to 24 hrs) of >100 mL. Single doses of 25 μg to 100 μg of Compound (II) triphenylacetate (containing lactose and magnesium stearate) demonstrated 24 hour duration of action as assessed by a 190 mL or greater increase in mean 23 to 24 hour post-dose FEV1 versus placebo).

Combination Therapy

A combination of Compound (I) bromide and Compound (II) triphenylacetate has been administered to sixteen healthy Japanese volunteers, aged 20 to 65, as part of a clinical trial to assess the safety, tolerability, pharmacokinetics and pharmacodynamics of single inhaled doses of Compound (I) bromide and Compound (II) triphenylacetate as monotherapies and in combination. This study was a randomised, double blind, placebo-controlled, four-way crossover study wherein subjects received a single dose of:

Compound (I) bromide (500 mcg dose),
Compound (II) triphenylacetate (50 mcg dose),
Compound (I) bromide (500 mcg dose) and Compound (II) triphenylacetate (50 mcg dose) concurrently, or
placebo at each of the four treatment periods. On enrolment into the study subjects were assigned to one of four treatment sequences based on a Williams design.

This clinical study in healthy Japanese volunteers, evaluated the effect of Compound (I) bromide (500 mcg dose) and Compound (II) triphenylacetate (50 mcg dose) administered as single inhaled doses and concurrently (Compound (I) bromide (500 mcg dose) and Compound (II) triphenylacetate (50 mcg dose)) on lung function parameters. Single inhaled doses and the combination administered using dry powder inhalers were found to be well tolerated. In this study $FEV_1$ values were recorded. $FEV_1$ values were higher for ail treatment groups compared with placebo. The group dosed with Compound (I) bromide (500 mcg dose) and Compound (II) triphenylacetate (50 mcg dose) concurrently showing the largest difference relative to placebo.

Pharmaceutical Formulations
Preparation of Blends
Compound (I) Bromide

Pharmaceutical grade α-lactose monohydrate, sourced from DMV Fronterra Excipients, complying with the requirements of Ph.Eur/USNF may be used. Before use, the α-lactose monohydrate may be sieved through a coarse screen (for example with a mesh size 500 or 800 microns). The level of fines in the α-lactose monohydrate, which can be measured by Sympatec, may be 4.5% w/w less than 4.5 micron.

Compound (I) bromide is micronised before use in an APTM microniser to give a mass median diameter of 1 to 5 microns, such as 2 to 5 microns.

Pharmaceutical grade magnesium stearate, sourced from Peter Greven, complying with the requirements of Ph.Eur/USNF may be used as supplied with a mass median particle size of 8 to 12 microns.

Blend A

Lactose monohydrate may be passed through a sieve and then combined with magnesium stearate and blended using either a high shear mixer (a QMM, PMA or TRV series mixer, such as TRV25 or TRV65) or a low shear tumbling blender (a Turbula mixer) to provide a magnesium stearate/lactose premix, hereinafter referred to as blend A.

Blend B

Final blend B may be obtained as follows. An quantity of blend A and compound (I) bromide may be screened, for example using a COMIL™, and then blended with the remaning blend A using either a high shear mixer (a QMM, PMA or TRV series mixer, such as TRV25 or TRV65) or a low shear tumbling blender (a Turbula mixer).

Representative Batch Formula for Compound (I) Bromide Powder Blend (62.5 microgram per blister)

| Ingredient | Quantity |
| --- | --- |
| Micronised Compound (I) Bromide | 74.1 g |
| Magnesium Stearate | 75 g |
| Lactose Monohydrate | To 12.5 kg |

Note:
74.1 g of Compound (I) Bromide is equivalent to 62.5 g of the free cation. The quantity of Compound (I) Bromide added may be adjusted to reflect the assigned purity of the input drug substance.

Representative Batch Formula for Compound (I) Bromide Powder Bland 125 microgram per blister)

| Ingredient | Quantity |
| --- | --- |
| Micronised Compound (I) Bromide | 148.3 g |
| Magnesium Stearate | 75 g |
| Lactose Monohydrate | To 12.5 kg |

Note:
148.3 g of Compound (I) Bromide is equivalent to 125 g of the free cation. The quantity of Compound (I) Bromide added may be adjusted to reflect the assigned purity of the input drug substance.

Blending Parameters (using a TRV25, 12.5 kg scale)

| Blend | Time (mins) | Approximate Speed (rpm) |
| --- | --- | --- |
| A | 6 | 460 |
| B | 10 | 590 |

Blister Strip Preparation

The blended composition may then be transferred into blister strips (typical nominal mean quantity of blend per blister is 12.5-13.5 mg) of the type generally used for the supply of dry powder for inhalation and the blister strips were sealed in the customary fashion.

Compound (II) Triphenylacetate

Pharmacetical grade α-lactose monohydrate, which can be sourced from DMV Fronterra Excipients, complying with the requirements of Ph.Eur/USNF may be used. Before use, the α-lactose monohydrate may be sieved through a coarse screen (typical mesh size 500 microns). The level of fines in the α-lactose monohydrate, which can be measured by Sympatec, may be 4.5% w/w less than 4.5 micron.

Compound (II) triphenylacetate is micronised before use in an APTM microniser to give a MMD (mass median particle diameter) of from 1 to 5 microns, such as 2 to 5 microns, for example 1.8 microns.

Pharmaceutical grade Magnesium stearate, which can be sourced from Peter Greven, complying with the requirements of Ph.Eur/USNF may be used as supplied with a mass median particle size 8 to 12 microns.

Blend A

Lactose monohydrate may be passed through a sieve and then combined with magnesium stearate (typically 130 g) and blended using either a high shear mixer (a QMM, PMA or TRV series mixer, such as TRV25 or TRV65) or a low shear tumbling blender (a Turbula mixer) to provide a magnesium stearate/lactose premix, hereinafter referred to as blend A.

Blend B

Final blend B may be obtained as follows. An appropriate quantity of blend A and compound (II) triphenylacetate (typically 5-165 g) may be screened, for example using a COMIL™, and then blended with the remaining blend A using either a high shear mixer (a QMM, PMA or TRV series mixer) or a low shear tumbling blender (a Turbula mixer). The final concentration of compound (II) triphenylacetate in the blends is typically in the range 0.02% w/w-0.8% w/w free base equivalent.

Blister Strip Preparation

The blended composition is transferred into blisterstrips (typical nominal mean quantity of blend B per blister is 12.5-13.5 mg) or the type generally used for the supply of dry powder for inhalation and the blister strips are then sealed in the customary fashion.

Example Preparations

Using the above-described procedure the following exemplary formulations may be prepared:

| Blend No | Mass of Magnesium stearate | Mass of compound (II) triphenylacetate (micronised) | Mass of lactose | Quantity per blister |
| --- | --- | --- | --- | --- |
| 1 | 130 g | 5.0 g | To 13 kg | 13 mg |
| 2 | 130 g | 10.3 g | To 13 kg | 13 mg |
| 3 | 130 g | 20.7 g | To 13 kg | 13 mg |
| 4 | 130 g | 41.3 g | To 13 kg | 13 mg |
| 5 | 130 g | 82.7 g | To 13 kg | 13 mg |
| 6 | 130 g | 165.4 g | To 13 kg | 13 mg |

Note:
The quantity of compound (II) triphenylacetate used is based on a base to salt conversion factor of 1.59. For example, 41 g of Compound (II) triphenylacetate is equivalent to 25 g of the free base.

Example Blending Parameters (using a TRV25, 13 kg scale, Compound (II) triphenylacetate powder blend (25 microgram blister))

| Blend | Time (mins) | Approximate Speed (rpm) |
| --- | --- | --- |
| A | 9 | 550 |
| B | 8.5 | 550 |

Example Dry Powder Inhaler Devices

Compound (I) bromide and Compound (II) triphenylacetate as an inhalation powder may be administered in a DPI device containing two blister strips. One strip contains a blend of micronised Compound (I) bromide (approximately 500 micrograms per blister), magnesium stearate and lactose monohydrate. The second strip contains blend of micronised Compound (II) triphenylacetate (approximately 25 micrograms per blister), magnesium stearate and lactose monohydrate. The DPI device will deliver, when actuated, the contents of a single blister simultaneously from each of the two blister strips. Each blister strip is a double foil laminate containing 30 blisters per strip.

In a further embodiment, Compound (I) bromide and Compound (II) triphenylacetate as an inhalation powder may be administered in a dry powder inhaler device containing two blister strips, wherein one strip contains a blend of micronised Compound (I) bromide (approximately 125 or 62.5 micrograms per blister), magnesium stearate (at an amount of 0.6% w/w of the total powder weight per blister) and lactose monohydrate. The second strip contains a blend of micronised Compound (II) triphenylacetate (approximately 25 micrograms per blister), magnesium stearate and lactose monohydrate. The second strip optionally further comprises 6α,9α-difluro-17α-[(2-furanylcarbonyl)oxy]-11β-hydroxy-16α-methyl-3-oxo-androsta-1,4-diene-17β-carbothioic acid S-fluoromethyl ester (fluticasone furoate) at an amount of approximately 100 micrograms per blister. The DPI device will deliver, when actuated, the contents of a single blister simultaneously from each of the two blister strips. Each blister strip is a double foil laminate containing 7, 14 or 30 filled blisters per strip.

In a further embodiment, Compound (I) bromide and Compound (II) triphenylacetate as an inhalation powder may be administered in a dry powder inhaler device containing two blister strips, wherein one strip contains a blend of micronised Compound (I) bromide (approximately 125 or 62.5 micrograms per blister), Compound (II) triphenylacetate (approximately 25 micrograms per blister), magnesium stearate and lactose monohydrate. The second strip contains a blend of 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) at an amount of approximately 100 micrograms per blister, and lactose monohydrate. The DPI device will deliver, when actuated, the contents of a single blister simultaneously from each of the two blister strips. Each list strip is a double foil laminated 7, 14 or 30 filled blisters per strip.

All publications, including but not limited to patents and patent applications, cited in this specification are herein incorporated by reference as if each in publication were specifically and individually indicated to be incorporated by reference herein as though fully set forth.

The above description full discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

The invention claimed is:

1. A method of treating chronic obstructive pulmonary disease in a human comprising: the once per day administration to the human of a pharmaceutical combination product, comprising:
   a) a compound of the formula:

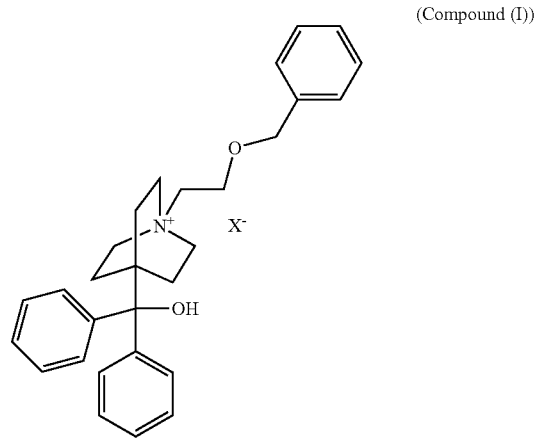

(Compound (I))

wherein X⁻ is a pharmaceutically acceptable anion, wherein Compound (I) is in an amount of about 62.5 mcg/dose in the combination product, and is in the form of a dry powder; and
   b) 4-{(1R)-2-[(6-{2-[(2,6-dichlorobenzyl)oxy] ethoxy}hexyl)amino]-1-hydroxyethyl}-2-(hydroxymethyl)phenol, or a pharmaceutically acceptable salt thereof (Compound (II)), wherein Compound (II) is in an amount of about 25 mcg/dosein the combination product, and is in the form of a dry powder;
   wherein Compounds (I) and (II) are presented in a form adapted for simultaneous administration.

2. The method according to claim 1, wherein for Compound (I) the pharmaceutically acceptable anion is selected from the group consisting of chloride, bromide, iodide, hydroxide, sulfate, nitrate, phosphate, acetate, trifluoroacetate, fumarate, citrate, oxalate, tartrate, succinate, mandelate, methanesulfonate or p-toluenesulfonate.

3. The method according to claim 2, wherein Compound (I) is 4-[hydroxy(diphenyl)methyl]-1-{2-[(phenylmethyl)oxy]ethyl}-1-azoniabicyclo[2.2.2] octane bromide.

4. The method according to claim 1, wherein Compound (II) is 4-{(1R)-2-[(6-{2-[(2,6-dichlorobenzyl)oxy] ethoxy}hexyl)amino]-1-hydroxyethyl}-2-(hydroxymethyl) phenol triphenylacetate.

5. The method according to claim 3, wherein Compound (II) is 4-{(1R)-2-[(6-{2-[(2,6-dichlorobenzyl)oxy] ethoxy}hexyl)amino]-1-hydroxyethyl}-2-(hydroxymethyl) phenol triphenylacetate.

6. The method according to claim 1, wherein the pharmaceutical product is in a form suitable for administration by inhalation via a medicament dispenser, wherein said medicametn dispenser is selected from the group consisting of a reservoir dry powder inhaler, a unit-dose dry powder inhaler, and a pre-metered multi-dose dry powder inhaler.

7. The method according to claim 6, wherein Compound (I) and Compound (II) are presented in (i) separate dry powder compositions or (ii) an admixed dry powder composition.

8. The method according to claim 7, wherein each separate dry powder composition or the admixed dry powder composition contains a carrier, which is lactose.

9. The method according to claim 8, wherein each seperate or the admixed composition contains a ternary agent.

10. The method according to claim 9, wherein the ternary agent is magnesium stearate.

11. The method according to claim 7, wherein said separate or admixed composition is in unit dose form, and further wherein the unit dose form is selected from the group consisting of a capsule, a cartridge and a blister.

12. The method according to claim 1, wherein the pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

13. The method according to claim 12, wherein the 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

14. The method according to claim 5, wherein the pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

15. The method according to claim 14, wherein the 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) is present in an amount of about 100 mcg/dose.

16. The method according to claim 5, wherein the pharmaceutical product is in a form suitable for administration by inhalation via a medicament dispenser, wherein said medicament dispenser is selected from the group consisting of a reservoir dry powder inhaler, a unit-dose dry powder inhaler, and a pre-metered multi-dose dry powder inhaler.

17. The method according to claim 16, wherein Compound (I) and Compound (II) are presented in (i) separate dry powder compositions or (ii) an admixed dry powder composition.

18. The method according to claim 17, wherein each separate dry powder composition or the admixed dry powder composition contains a carrier, which is lactose.

19. The method according to claim 18, wherein each seperate or the admixed composition contains a ternary agent.

20. The method according to claim 19, wherein the ternary agent is magnesium stearate.

21. The method according to claim 17, wherein said separate or admixed composition is in unit dose form, and further wherein the unit dose form is selected from the group consisting of a capsule, a cartridge and a blister.

22. A method of treating chronic obstructive pulmonary disease (COPD) in a human comprising:

simultaneously administering, via inhalation, to said human, once per day, a pharmaceutical combination product comprising:

a) a first dry powder composition comprising:

(i) about 62.5 mcg/dose of a compound of the formula:

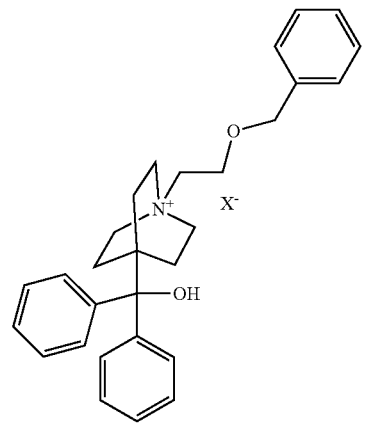

(Compound (I))

wherein $X^-$ is a pharmaceutically acceptable anion;
(ii) lactose; and
(iii) magnesium stearate in an amount of about 0.6% w/w of said first dry powder composition; and b) a second dry powder composition comprising:

(i) about 25 mcg/dose of 4-{(1R)-2-[(6-{2-[(2,6-dichlorobenzyl)oxy]ethoxy}hexyl)amino]-1-hydroxyethyl}-2-(hydroxymethyl)phenol, or a pharmaceutically acceptable salt thereof (Compound (II));
(ii) lactose; and
(iii) magnesium stearate in an amount of about 1.0% w/w of said second dry powder composition.

23. The method according to claim 22, wherein for Compound (I), the pharmaceutically acceptable anion is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

24. The method according to claim 23, wherein for Compound (I) the pharmaceutically acceptable anion is bromide.

25. The method according to claim 22, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

26. The method according to claim 24, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

27. The method according to claim 22, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) present in an amount of about 100 mcg/dose.

28. The method according to claim 23, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) present in an amount of about 100 mcg/dose.

29. The method according to claim 24, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) present in an amount of about 100 mcg/dose.

30. The method according to claim 25, wherein pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate) present in an amount of about 100 mcg/dose.

31. A method of treating chronic obstructive pulmonary disease (COPD) in a human comprising:
simultaneously administering, via inhalation, to said human, once per day, a pharmaceutical combination product comprising:
a) a first dry powder composition comprising:
(i) about 62.5 mcg/dose of a compound of the formula:

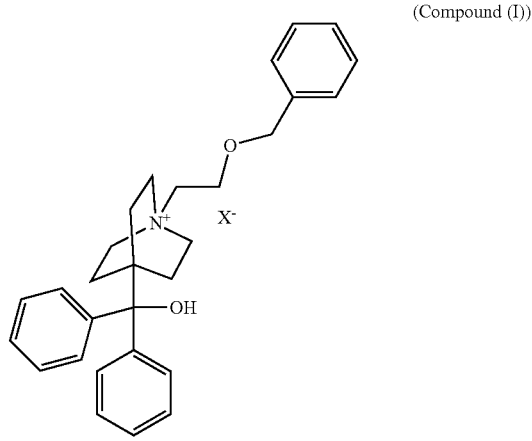

(Compound (I))

wherein X$^-$ is a pharmaceutically acceptable anion;
(ii) about 25 mcg/dose 4-{(1R)-2-[(6-{2-[(2,6-dichlorobenzyl)oxy]ethoxy}hexyl)amino]-1-hydroxyethyl}-2-(hydroxymethyl)phenol, or a pharmaceutically acceptable salt thereof (Compound (II));
(iii) carrier excipient; and
(iv) a ternary agent, and
(b) a second dry powder composition comprising:
(i) 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), present in an amount of about 100 mcg/dose; and
(ii) carrier excipient.

32. The method according to claim 31, wherein for Compound (I), the pharmaceutically acceptable anion is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate or p-toluenesulfonate.

33. The method according to claim 32, wherein for Compound (I) the pharmaceutically acceptable anion is bromide.

34. The method according to claim 31, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

35. The method according to claim 33, wherein Compound (II) is 4-{(1R)-2-[(6-{2-[(2,6-dichlorobenzyl)oxy]ethoxy}hexyl)amino]-1-hydroxyethyl}-2-(hydroxymethyl)phenol triphenylacetate.

36. The method of claim 31, wherein the carrier excipient comprises lactose, and the ternary agent comprises magnesium stearate.

37. The method of claim 36, wherein the pharmaceutical combination product is administered via a medicament dispenser, wherein said medicament dispenser is selected from the group consisting of a reservoir dry powder inhaler, a unit-dose dry powder inhaler, and a pre-metered multi-dose dry powder inhaler.

38. The method according to claim 37, wherein each of said first and second dry powder compositions is in unit dose form, wherein said unit dose forms are independently selected from the group consisting of a capsule, a cartridge and a blister.

39. The method of claim 35, wherein the carrier excipient comprises lactose, and the ternary agent comprises magnesium stearate.

40. The method of claim 39, wherein the pharmaceutical combination product is administered via a medicament dispenser, wherein said medicament dispenser is selected from the group consisting of a reservoir dry powder inhaler, a unit-dose dry powder inhaler, and a pre-metered multi-dose dry powder inhaler.

41. The method according to claim 40, wherein each of said first and second dry powder compositions are in unit dose form, wherein said unit dose forms are indepenently selected from the group consisting of a capsule, a cartridge and a blister.

42. The method according to claim 10, wherein the ternary agent is magnesium stearate, present in an amount of about 0.6% w/w of a composition of Compound (I).

43. The method according to claim 10, wherein the ternary agent is magnesium stearate, present in an amount of about 1.0% w/w of a composition of Compound (II).

44. The method according to claim 10, wherein the ternary agent is magnesium stearate, present in an amount of about 0.6% w/w of a composition of Compound (I) and in an amount of about 1.0% w/w of a composition of Compound (II).

45. The method according to claim 20, wherein the ternary agent is magnesium stearate, present in an amount of about 0.6% w/w of a composition of Compound (I).

46. The method according to claim 20, wherein the ternary agent is magnesium stearate, present in an amount of about 1.0% w/w of a composition of Compound (II).

47. The method according to claim 20, wherein the ternary agent is magnesium stearate, present in an amount of about 0.6% w/w of a composition of Compound (I) and in an amount of about 1.0% w/w of a composition of Compound (II).

48. The method according to claim 20, wherein the pharmaceutical combination product further comprises 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate).

49. The method according to claim 48, wherein the fluticasone furoate is present in an amount of about 100 mcg/dose.

50. The method of claim 48, wherein the pharmaceutical combination product is administered via a medicament dispenser, wherein said medicament dispenser is selected from the group consisting of a reservoir dry powder inhaler, a unit-dose dry powder inhaler, and a pre-metered multi-dose dry powder inhaler.

51. The method according to claim 50, wherein Compound (I) and Compound (II) are presented in (i) separate dry powder compositions or (ii) an admixed dry powder composition.

52. The method according to claim 51, wherein each separate dry powder composition or the admixed dry powder composition contains a carrier, which is lactose.

53. The method according to claim 52, wherein each separate or the admixed composition contains a ternary agent.

54. The method according to claim 53, wherein the ternary agent is magnesium stearate.

55. The method according to claim 54, wherein the magnesium stearate is present in a composition comprising Compound (II), in an amount of about 1.0% w/w of the composition comprising Compound (II).

56. The method according to claim 49, wherein said dry powder compositions are in unit dose form, wherein each of said unit dose forms are independently selected from the group consisting of a capsule, a cartridge or a blister.

* * * * *